United States Patent
Fisher et al.

(10) Patent No.: US 12,402,868 B1
(45) Date of Patent: Sep. 2, 2025

(54) ROBOTIC ENDOSCOPY SYSTEM

(71) Applicant: Praxis Holding LLC, Tampa, FL (US)

(72) Inventors: John S. Fisher, Belleair, FL (US); Elizabeth F. Maynard, Tampa, FL (US); James Lee, Vista, CA (US)

(73) Assignee: Praxis Holding LLC, Tampa, FL (US)

( * ) Notice: Subject to any disclaimer, the term of this patent is extended or adjusted under 35 U.S.C. 154(b) by 0 days.

(21) Appl. No.: 19/006,540

(22) Filed: Dec. 31, 2024

(51) Int. Cl.
*A61B 10/02* (2006.01)
*A61B 34/30* (2016.01)
*A61B 90/00* (2016.01)

(52) U.S. Cl.
CPC .......... *A61B 10/0283* (2013.01); *A61B 34/30* (2016.02); *A61B 90/06* (2016.02); *A61B 2034/305* (2016.02); *A61B 2090/066* (2016.02)

(58) Field of Classification Search
CPC ............... A61B 10/0283; A61B 34/30; A61B 2034/301; A61B 2034/305; A61B 90/06; A61B 2090/066
See application file for complete search history.

(56) References Cited

U.S. PATENT DOCUMENTS

| | | | |
|---|---|---|---|
| 2015/0080907 A1* | 3/2015 | Herrell ................. | A61B 1/0016 606/130 |
| 2021/0030496 A1* | 2/2021 | Devengenzo .......... | A61B 34/30 |
| 2021/0196251 A1* | 7/2021 | Dull .................. | A61M 25/0102 |
| 2021/0282755 A1* | 9/2021 | Ramamurthy ..... | A61B 10/0266 |
| 2025/0017449 A1* | 1/2025 | Boader ............. | A61B 1/00149 |

* cited by examiner

*Primary Examiner* — Devin B Henson
(74) *Attorney, Agent, or Firm* — Nicholas Pfeifer; Smith & Hopen, P. A.

(57) ABSTRACT

A robotic medical device designed for tissue extraction, featuring a modular construction and motion control assembly. The system includes a robotic arm with multiple joints providing at least three degrees of freedom, a main body with a motorized vacuum pump, and a user interface for operational control. A needle assembly, secured within a removable proximal hub, incorporates a hollow needle with one or more cutting features, a geared wheel for transmitting oscillatory and translational motion, and a luer hub with an O-ring to maintain vacuum pressure. A suction tube connects the needle assembly to the vacuum pump, maintaining negative pressure. The device includes features such as a disposable and reusable elements, quick-connect mechanisms, and integrated sensors for monitoring motion and pressure.

18 Claims, 21 Drawing Sheets

ROBOTIC ENDOSCOPY SYSTEM

BACKGROUND OF THE INVENTION

1. Field of the Invention

This invention relates, generally, to medical devices. More specifically, it relates to a robotic platform for controlling a biopsy syringe.

2. Brief Description of the Prior Art

The accurate diagnosis of various medical conditions, including cancer, often requires obtaining tissue samples through biopsy procedures. Biopsies involve the extraction of tissue from a suspected site within the body for histopathological analysis. Current approaches to performing biopsies typically fall into one of two categories: manual and semi-automated. While these methods have seen significant advancements, they still present notable challenges that impact procedural accuracy, efficiency, and patient outcomes.

Manual biopsy techniques rely heavily on the clinician's skill and experience. This approach involves visual or imaging guidance, such as ultrasound or CT scans, to position a biopsy needle at the target site. In addition, the clinician needs to manipulate the needle in a specific manner to capture tissue from the target site. Despite the widespread use of these methods, there are inherent limitations. Precise targeting and acquisition can be difficult, particularly for deep-seated or small lesions, due to natural physiological movement (e.g., breathing or heartbeat) or limited visibility in imaging modalities. This lack of precision can lead to inadequate or inaccurate sampling, requiring repeat procedures and causing additional discomfort to patients.

Semi-automated biopsy systems incorporate devices designed to assist in needle insertion and sample collection. These devices often include mechanisms to improve needle stabilization or provide mechanical assistance during the biopsy. However, these systems still rely heavily on manual operation for needle placement and alignment. The lack of real-time adaptive feedback and precision limits their utility in complex procedures, especially in cases requiring millimeter-level accuracy.

The emergence of robotic-assisted medical technologies has highlighted the potential to address the deficiencies of traditional biopsy techniques. Robotic systems offer unparalleled control, precision, and stability in minimally invasive procedures. Despite these advantages, the integration of robotic systems into biopsy procedures remains underexplored due to inherent challenges associated with integration of biopsy technology and the considerations of multi-use components, replacement components, and ease of use.

Accordingly, what is needed is a robot-controlled biopsy needle system that combines multi-directional movement control with advanced imaging and feedback mechanisms. This innovation represents a significant step forward in the field of medical diagnostics, offering a solution to the challenges of precision, consistency, and procedural safety that have long plagued biopsy practices. However, in view of the art considered as a whole at the time the present invention was made, it was not obvious to those of ordinary skill in the field of this invention how the shortcomings of the prior art could be overcome.

SUMMARY OF THE INVENTION

The long-standing but heretofore unfulfilled need for an advanced robotic biopsy device that combines oscillatory and translational movement is now met by a novel and non-obvious invention disclosed and claimed herein.

The present invention includes a robotic medical device comprising a needle assembly that includes a hollow needle, a needle gear at the proximal end of the hollow needle, and a luer hub with an O-ring, wherein the needle is configured to rotate relative to the luer hub. The invention further includes a robotic arm including multiple joints providing at least three degrees of freedom, a translation guide and a needle translator configured to axially translate the needle assembly along the length of the translation guide, a motor operably engaging the needle gear to rotate the needle about its longitudinal axis, and a tissue chamber established at least in part by a hollow interior of the needle and in fluidic communication with a vacuum source via a suction tube. The needle is configured to be axially translated and rotated relative to its longitudinal axis while the tissue chamber is subject to the vacuum.

In an embodiment, the invention further comprises a proximal hub configured to house the needle assembly and temporarily attach to the needle translator. The proximal hub comprises a removable attachment mechanism, a luer hub retention latch, an interface for transferring oscillatory and translational motion from the motor to the geared wheel, and an anti-buckling tube.

In an embodiment, the invention further comprises a distal hub configured to be temporarily coupled to the terminal joint of the robotic arm. The distal hub comprises a removable attachment mechanism, a sheath clamping latch, a guide tube, and an endoscope.

In an embodiment, the needle assembly and suction tube are disposable. In an embodiment, the robotic arm includes a detachable joint mechanism with alignment pins and a quick-release locking collar to facilitate removal and reattachment.

In an embodiment, the invention further includes sensors, including a position sensor configured to monitor the movement of the robotic arm, a pressure sensor configured to monitor vacuum levels within the tissue chamber, and a force-torque feedback sensor to monitor the rotation and translation of the needle.

In an embodiment, the invention includes a robotic medical device comprising a needle assembly that includes a hollow needle and a needle gear disposed near the proximal end of the needle. The invention further includes a robotic arm, the robotic arm including a translation guide and a needle translator, a proximal hub configured to house the needle and temporarily attach to the needle translator, a motor configured to operably engage the needle gear to rotate the needle about its longitudinal axis, and a distal hub configured to be temporarily coupled to the terminal joint of the robotic arm. The needle translator is configured to translate the needle through the distal hub and translate the proximal hub towards the distal hub. The distal hub includes a passage for receiving the needle, the needle including a tissue chamber established at least in part by the hollow interior of the needle and in fluidic communication with a vacuum source via a suction tube. The needle is configured to be axially translated and rotated relative to its longitudinal axis while the tissue chamber is subject to a vacuum.

In an embodiment, the proximal hub comprises a removable attachment mechanism, a luer hub retention latch, and an interface for transferring oscillatory and translational motion from the motor to the geared wheel.

In an embodiment, the invention further includes an anti-buckling tube extending at least partially between the distal hub and the proximal hub, wherein the anti-buckling tube has greater rigidity than the needle.

In an embodiment, the distal hub comprises a removable attachment mechanism, a sheath clamping latch, a guide tube, and an endoscope.

In an embodiment, the needle assembly and suction tube are disposable.

In an embodiment, the robotic arm includes a detachable joint mechanism with alignment pins and a quick-release locking collar to facilitate removal and reattachment.

In an embodiment, the device further comprises sensors, including a position sensor configured to monitor movement of the robotic arm, a pressure sensor configured to monitor vacuum levels within the tissue chamber, and a force-torque feedback sensor configured to monitor the rotation and translation of the needle.

In an embodiment, the invention provides a robotic medical device comprising a needle assembly that includes a hollow needle, a needle gear disposed proximate to the proximal end of the needle, a robotic arm including a translation guide and a needle translator, a proximal hub configured to house the needle and temporarily attach to the needle translator, a motor operably engaging the needle gear to rotate the needle about its longitudinal axis, and a distal hub temporarily coupled to the terminal joint of the robotic arm, wherein the distal hub includes a passage for receiving the needle. The needle translator is configured to translate the needle through the distal hub and translate the proximal hub towards the distal hub. The tissue chamber is established at least in part by the hollow interior of the needle and is in fluidic communication with a vacuum source. The needle is configured to be axially translated and rotated relative to its longitudinal axis while the tissue chamber is subject to a vacuum.

In an embodiment, the proximal hub comprises a removable attachment mechanism, a luer hub retention latch, and an interface for transferring oscillatory and translational motion from the motor to the geared wheel.

In an embodiment, the device further includes an anti-buckling tube extending at least partially between the distal hub and the proximal hub, wherein the anti-buckling tube has greater rigidity than the needle.

In an embodiment, the distal hub comprises a removable attachment mechanism, a sheath clamping latch, a guide tube, and an endoscope.

In an embodiment, the device further comprises sensors, including a position sensor configured to monitor movement of the robotic arm, a pressure sensor configured to monitor vacuum levels within the tissue chamber, and a force-torque feedback sensor configured to monitor the rotation and translation of the needle.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not restrictive.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that one skilled in the art will recognize that other embodiments may be utilized, and it will be apparent to one skilled in the art that structural changes may be made without departing from the scope of the invention.

As such, elements/components shown in diagrams are illustrative of exemplary embodiments of the disclosure and are meant to avoid obscuring the disclosure. Any headings, used herein, are for organizational purposes only and shall not be used to limit the scope of the description or the claims.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," "in embodiments," "in alternative embodiments," "in an alternative embodiment," or "in some embodiments" in various places in the specification are not necessarily all referring to the same embodiment or embodiments. The terms "include," "including," "comprise," and "comprising" shall be understood to be open terms and any lists that follow are examples and not meant to be limited to the listed items.

The present invention includes a robotic medical device designed for tissue extraction, featuring a modular construction and motion control assembly. The system includes a robotic arm with multiple joints providing at least three degrees of freedom, a main body with a motorized vacuum pump, and a user interface for operational control. The system further includes a needle assembly configured to rotate and translate the needle while maintaining a vacuum through the needle. The device includes features such as a disposable and reusable elements, quick-connect mechanisms, and integrated sensors for monitoring motion and pressure.

Figure 1:
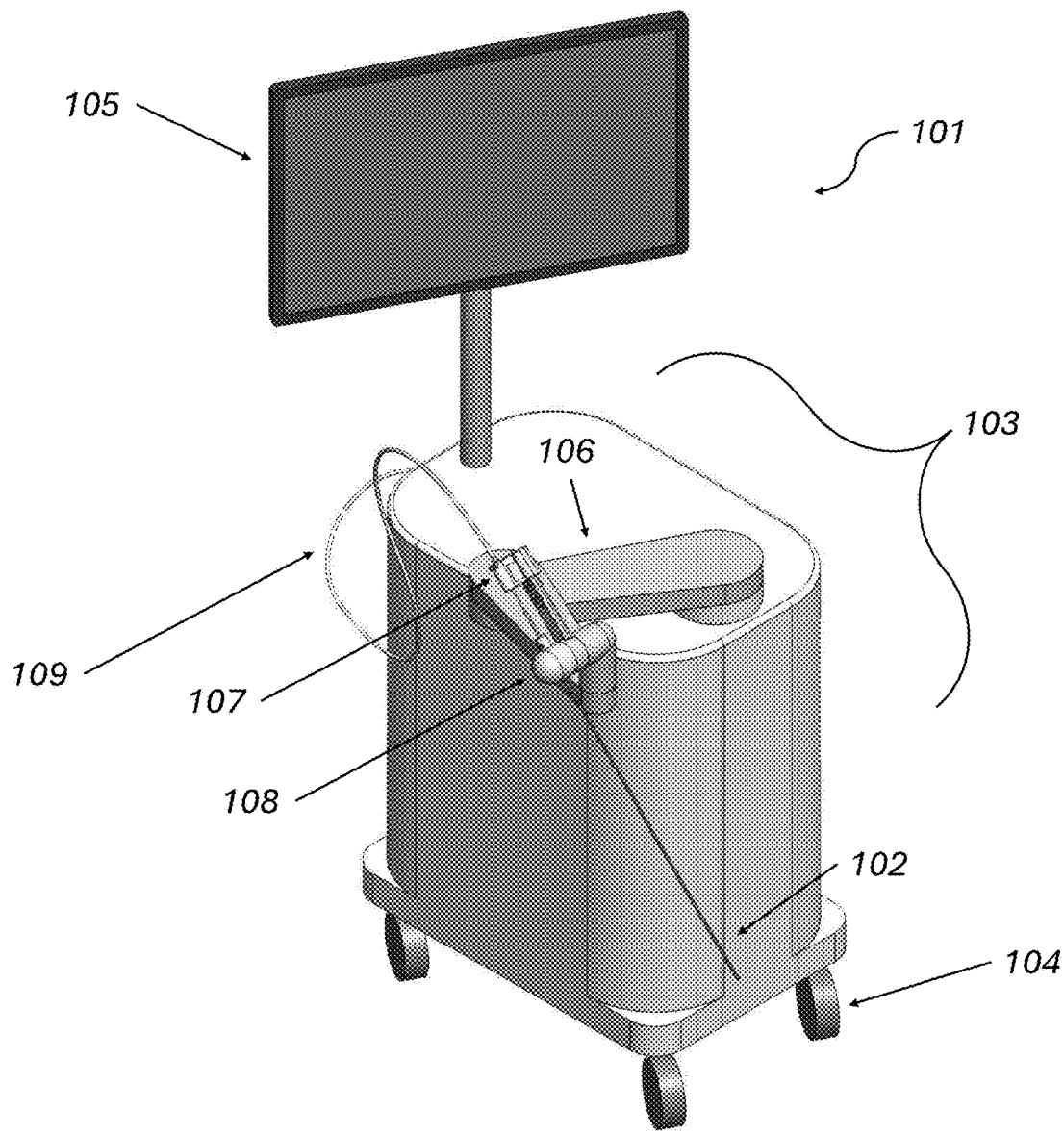
FIG. 1 is a perspective view of an embodiment of the present invention.

Referring now to FIG. 1, the present invention includes a robotic medical device 101 for manipulation of a needle 102 used in medical procedures. The needle 102 may be a hollow metal hypodermic needle of a size of between 18 to 27 gauge, and more particularly 22-25 gauge. The tip of the needle 102 is sharpened to facilitate cutting tissue when the needle 102 is advanced into tissue and rotated. The needle may also include cutting features disposed in the lateral side walls of the needle for cutting and extracting tissue.

The device 101 includes a main body 103 that serves as the central structural and functional unit of the device 101. The main body 103 is configured to securely house and protect the system's internal components while providing a stable base for interfacing with modular components. The device 101 is mounted on wheels 104 or other appropriate method of locomotion that allows the device to be moved and secured at a desired location.

The main body 103 also houses a power management system that includes a power supply unit that converts input power—whether from an AC source or a battery—into the required voltages for the platform's various subsystems. Voltage regulators may be integrated to maintain consistent output levels, protecting sensitive components from power surges or fluctuations.

Additionally, the main body 103 incorporates ventilation channels and thermal management features, including heat sinks and strategically placed fans, to maintain optimal operating temperatures for sensitive electronic components. The main body 103 also includes integrated cable management systems, allowing for secure and organized routing of electrical connections to minimize interference and improve system reliability.

In some embodiments, the present invention includes a user interface 105 securely connected to the main body 103 that serves as the primary input and output device, allowing the user to control the platform's functions and monitor system status in real time. The user interface 105 may include but is not limited to a touch screen, physical controls mounted on the main body, a handheld controller, and remote operating interface. However, it is contemplated that alternative user interface control devices can be used.

The present invention further includes a vacuum system. The vacuum pump is configured to generate negative pressure for tissue extraction. The vacuum system may be housed within the main body 103 and include suction tubing 109 in fluidic communication with the needle 102 to aid in the extraction of tissue. In an embodiment, the vacuum system may operate under programmable control to modulate suction levels based on procedural requirements. In an embodiment, integrated pressure sensors monitor the system in real time, providing feedback to maintain suction levels and alerting the user to any anomalies.

Figure 2:
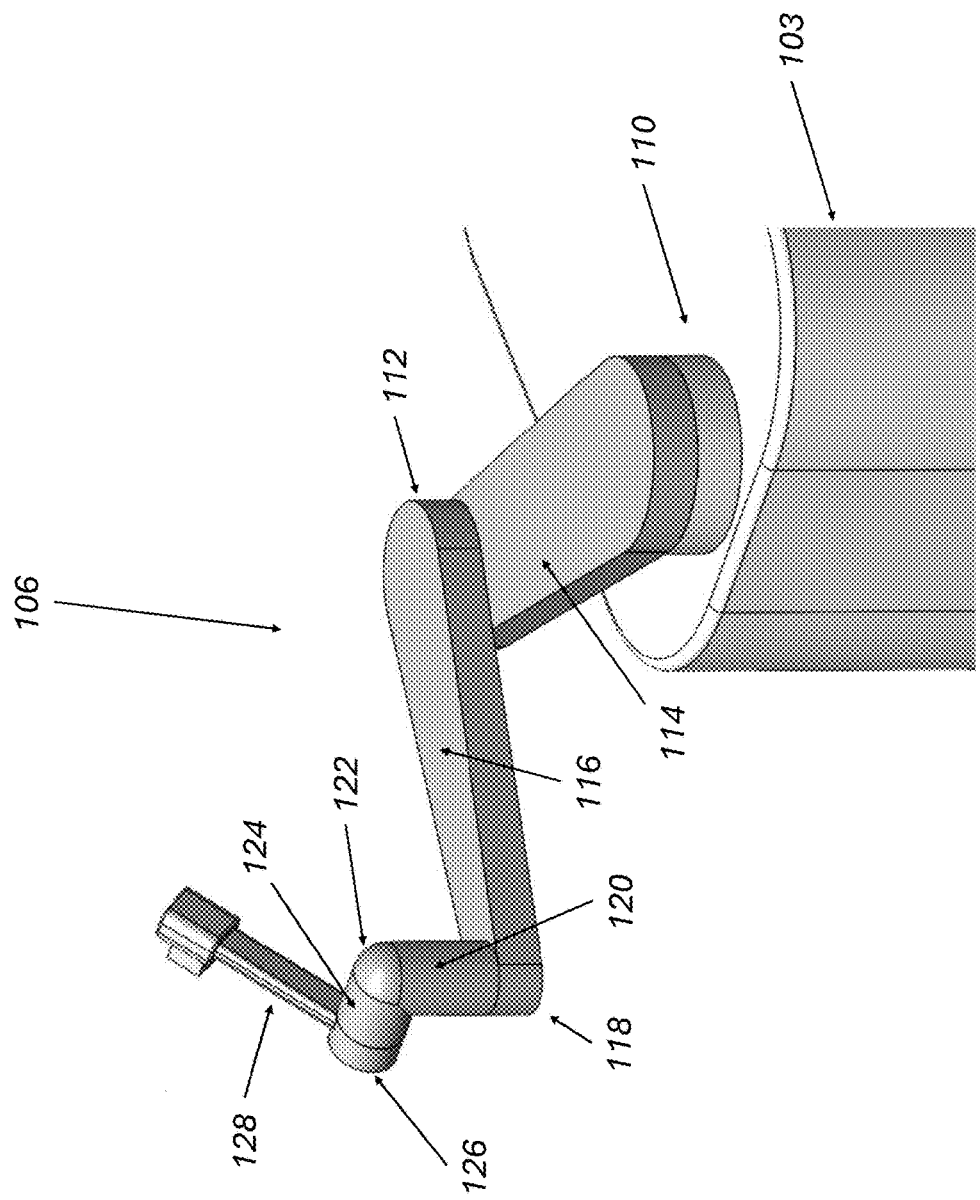
FIG. 2 is a close-up perspective view of an embodiment of the robotic arm.

As best depicted in FIG. 2, the present invention further includes a multi-segmented, articulated robotic arm assembly 106 that is mechanically coupled to the main body 103 at an appropriate position to allow complete freedom of movement without interfering with other components. The needle 102 is mechanically coupled to the distal end of the arm assembly 106 through a removable proximal hub 107 and removable distal hub 108. The arm assembly 106 is designed with multiple joints that may provide rotational, vertical, and horizontal motion. In an embodiment, the articulations are configured to allow complete rotational freedom.

In some embodiments, the robotic arm assembly 106 rotatably attached to the main body 103 at a base joint 110. In one embodiment, the base joint 110 can be configured for detachment from the main body through a modular quick-release system. The arm assembly 106 consists of a series of rigid segments, each connected by joints allowing for movement along at least one of the x-, y-, and z-axis. The joints may include adjustable locking or damping systems to stabilize the arm in its desired position when movement is complete. The base joint 110 connects the proximal end of the arm assembly 106 to the main body 103 and may provide rotational freedom of the arm assembly 106 around the vertical axis.

A shoulder joint 112 is positioned at the distal end of a first segment 114 of the arm assembly 106, providing a second point of rotation about the vertical axis of the shoulder joint 112. The configuration allows a second segment 116 of the robot arm assembly 106 to move along its horizontal plane, parallel to the first segment 114. In some embodiments, the shoulder joint 112 is configured to rotate about its horizontal axis allowing the second segment 116 to move along its vertical plane.

The shoulder joint 112 can be configured as a permanent joint including but not limited to a slewing ring bearing, turntable bearing, rotary coupling, or any other device or mechanism allowing full rotation of the joint. However, in some embodiments, the shoulder joint 112 is configured with a detachable mechanism, allowing the arm to be removed for cleaning and maintenance.

The arm assembly 106 may further include an elbow joint 118 coupled to the distal end of the second segment 116 of the robot arm assembly 106. The elbow joint 118 connects to the proximal end of a third segment 120 of the robot arm assembly 106, allowing rotation along the vertical axis of the third segment 120. In another embodiment, the elbow joint 118 is configured to rotate about its horizontal axis allowing the third segment 120 to move along its vertical plane. The elbow joint 118 can be configured as a permanent joint or as a detachable mechanism.

The distal end of the third segment 120 is connected to a wrist joint 122. The wrist joint 122 is connected to the proximal end of a fourth segment 124 of the robot arm, allowing multi-directional movement of the fourth segment 124. The wrist joint 122 can include but is not limited to a ball-and-socket joint, a multi-directional gimbal, a spherical bearing, or any other mechanism supporting multi-directional movement. The wrist joint 122 can be configured as a permanent joint or as a detachable mechanism. In an embodiment, the robot arm may include multiple wrist joints 122.

A terminal joint 126 is connected to the distal end of the fourth segment 124. The terminal joint is connected to the proximal end of a translation guide 128, allowing rotation about the horizontal axis of the terminal joint and moving the translation guide 128 rotationally along its vertical plane. In an embodiment, the terminal joint 126 is configured to rotate about its vertical axis allowing the translation guide 128 to move along its horizontal plane. The terminal joint 126 can be configured as a permanent joint or as a detachable mechanism.

In an embodiment, movement of the robotic arm joints is powered by a collection of actuators. The actuators can include but are not limited to DC or servo motors, pneumatic drive, hydraulic systems, or any other mechanism capable of precisely moving the robotic arm. For example, each actuator can be coupled to one or more gears that are configured to move the arm segments.

In an embodiment, a complex of sensors is coupled to the arm assembly 106 to measure and control arm function and the environment. To measure and maintain the position of the arm assembly 106, the present invention may include one or more sensors for gauging the orientation of the arm. These sensors may be connected to one or more sections of the arm assembly 106 and/or located at the distal end of the arm assembly 106. Non-limiting examples of such sensors include encoders, inertial measurement units (IMUs), force and torque sensors, optical motion tracking systems, ultrasonic sensors, LIDAR sensors, RADAR sensors, proximity sensors (capacitive or inductive), and vision systems with depth-sensing cameras.

In some embodiments, one or more additional sensors may be coupled to the arm assembly 106 at a position to allow the force exerted by and on the robotic arm to be measured. In an embodiment, sensors may be coupled to the arm assembly 106 to track the environment surrounding the device 101. In an embodiment, a camera can be connected to the distal end of the robot arm assembly 106 to track position during translation of the needle.

Figure 3:
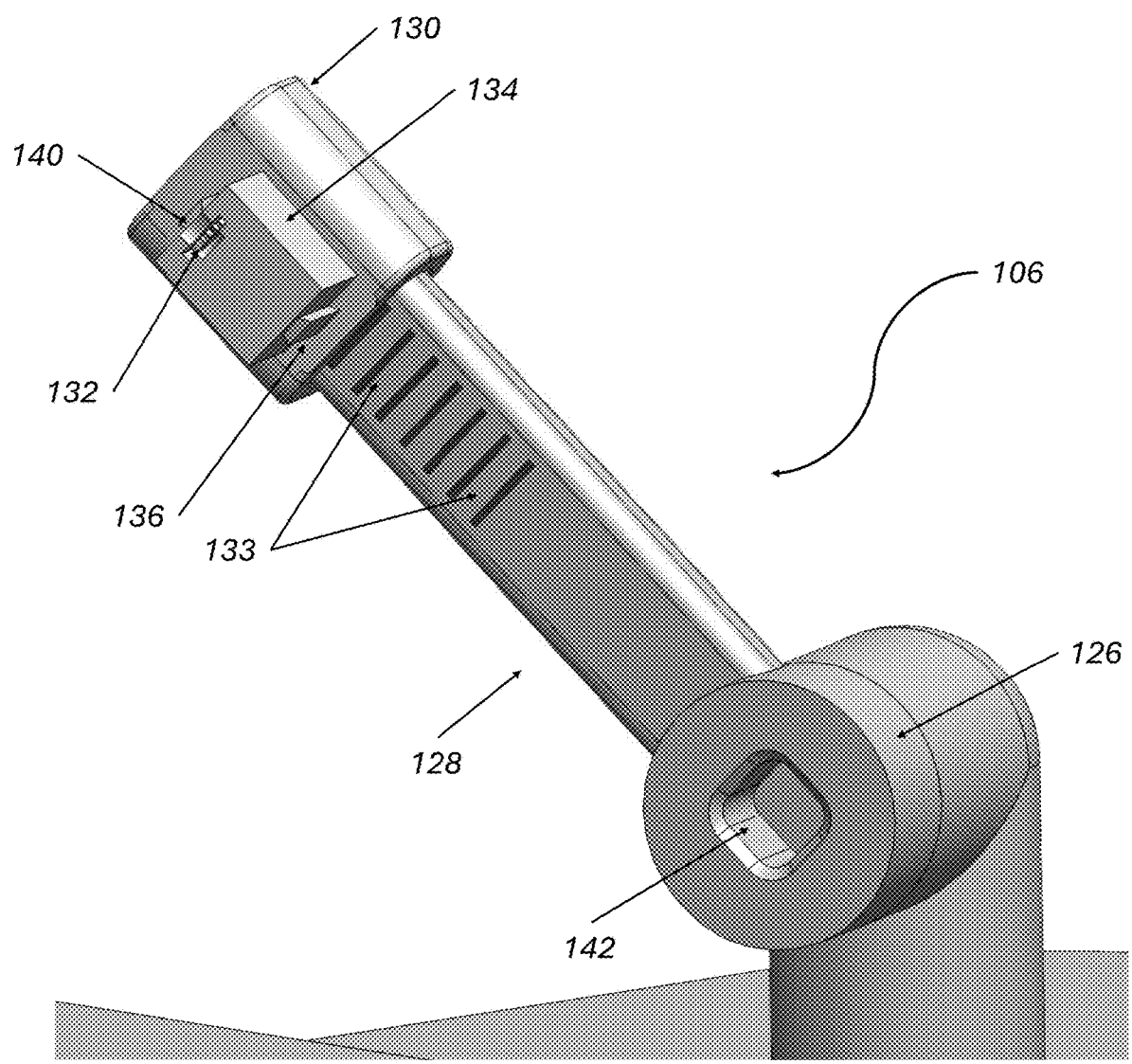
FIG. 3 is a focused view of the distal portion of the robot arm, including the terminal joint and distal housing unit.

Referring now to FIG. 3, embodiments of the present invention further include a needle translation mechanism 130 mechanically coupled to the distal end of robot arm assembly 106 for communication with and control of the needle 102. In some embodiments, needle translator 130 includes a channel configured to receive the translation guide 128, thereby allowing needle translator 130 to move along the length of the translation guide 128.

In some embodiments, the needle translator 130 includes a sliding/translation mechanism that is configured to cause translation of the needle translator 130 about the length of the translation guide 128. Non-limiting examples of translation mechanisms include lead screws, ball screws, rack and pinion systems, linear actuators, pneumatic cylinders, hydraulic cylinders, belt and pulley systems, chain drives, cam-driven mechanisms, and magnetic linear drives. However, alternative mechanisms can be used to effect translation of the needle translator 130 about the length of the translation guide 128.

In some embodiments, the translation mechanism is configured to engage the detents 133 along the arm's length. These detents 133 function as locking channels, allowing the needle translator 130 to be secured at various positions along the translation guide 128 depending on the procedural requirements. A built-in locking mechanism, including but not limited to spring-loaded pin or a clamping latch, ensures that the needle translator 130 remains firmly in place at a chosen detent 133. However, it is contemplated that alternative mechanisms for securing the arm assembly 106 in place during operation can be used.

In some embodiments, the needle translator 130 contains a needle rotator that is configured to cause rotation of the needle 102 about the longitudinal axis of the needle. In some embodiments, the needle rotator includes a gearing system in operable communication with a motor (all housed within the needle translator 130). The needle rotator includes an exposed gear 132 that is configured to mesh with the needle 102 or a needle hub to cause rotation of the needle 102.

In some embodiments, the needle rotator is configured to cause both axial translation and oscillatory rotation of the needle 102. To effect simultaneous rotational oscillation and axial translation, the needle rotator may include a secondary motor that engages a gear mechanism to cause back and forth translation of the needle as the needle rotates. Non-limiting examples include a gear train or eccentric cam mechanism, enabling controlled high-frequency back-and-forth translation of the needle during rotation to enhance tissue extraction. Alternatively, the needle translator 130 is configured to translate in an axial direction as the needle is rotated by the needle rotator.

In some embodiments, the needle translator 130 further includes an extended support structure 134 that is positioned perpendicularly to the translation guide 128 and provides a point of attachment for the proximal hub 107. The exposed gear 132 is mechanically coupled to the extended support structure 134 of the needle translator 130 and extends out of the extended support structure 134 to operably engage the needle 102 when the proximal hub 107 is secured to the needle translator 130.

The needle translator 130 may also include a mounting mechanism 136 to securely receive the proximal hub 107. As depicted, the mounting mechanism 136 is in the form of a male dovetail guide system that is configured to engage a corresponding dovetail receipt 152 for connecting to the proximal hub 107. However, alternative mechanisms and shapes may be used to ensure that the mounting mechanism 136 can securely and/or temporarily engage the proximal hub 107.

In some embodiments, the extended support structure 134 further includes a recess 140 located at an upper end of the extended support structure 134. The recess 140 is shaped and sized to receive a portion of the needle 102 and/or the needle hub. In addition, recess 140 provides sufficient clearance to allow for rotation of the needle 102 relative to the extended support structure 134.

The terminal joint 126 may include a securing mechanism 142 to receive and secure the removable distal hub 108 prior to operation. The securing mechanism 142 may include but is not limited to a key-hole slot or a dovetail guide. However, it is contemplated that alternative mechanisms for securing the removable distal hub 108 can be used. In an embodiment, the securing mechanism 142 is positioned in line with the extended support structure 134 of the needle translator 130 that houses the needle rotator.

In some embodiments, securing mechanism 142 has a design or shape to prevent rotation of the distal hub 108 relative to the terminal joint 126. The terminal joint is configured to rotate relative to other portions of the arm assembly 106, but not relative to the distal hub 108. Thus, the connection of the distal hub 108 to the securing mechanism may be in a form that prevents relative rotation of the distal hub 108 with respect to the terminal joint 126.

Figure 4:
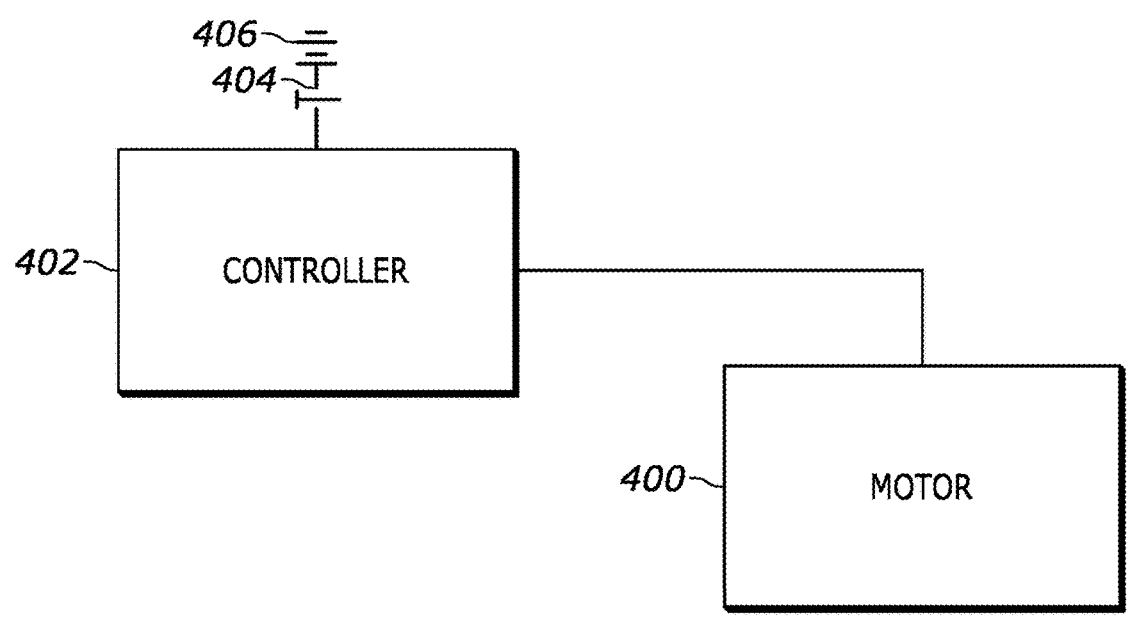
FIG. 4 is a block diagram of an embodiment of a first motor control circuit in which oscillation of the motor is effected by timing.

Now referring to FIG. 4, the present invention includes one or more motors 400, such as any of the motors described herein and known in the art, and one or more controllers 402, such as any of the controllers described herein and known in the art to operably control the motors. While the figure depicts a single motor and a single controller, it should be understood that the present invention may include multiple motors and/or multiple controllers to control the location of the arm segments, the translation of the needle, and/or the rotation of the needle. For the sake of brevity, the description related to the communication of the controllers and motors will reference a single controller and a single motor.

Motor 400 is in operable communication with a controller 402. The present invention may also include one or more motor switches 404. These components are in operable communication with each other and one or more batteries 406.

Figure 5:
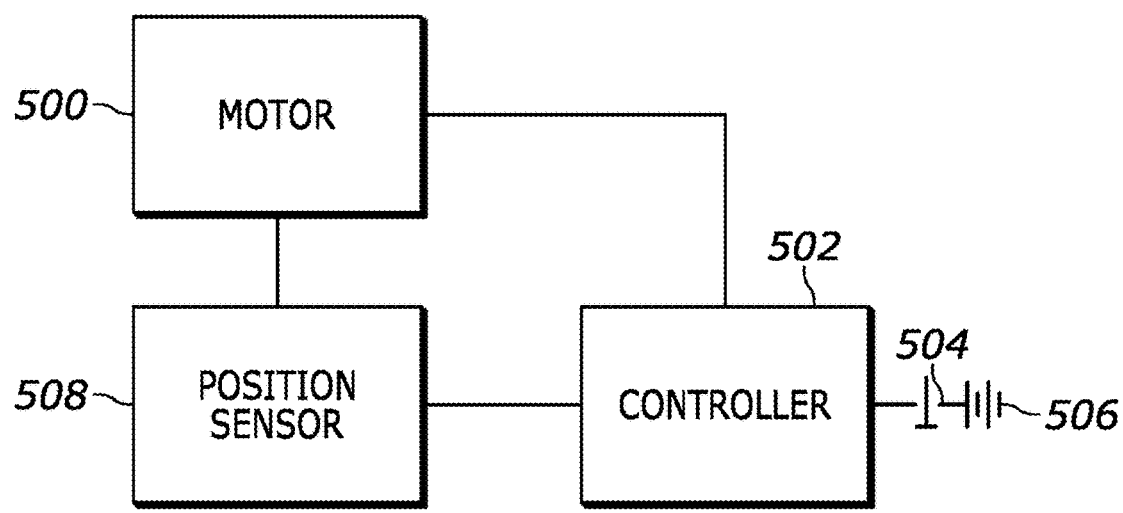
FIG. 5 is a block diagram of a first motor control circuit in which oscillation of the motor is effected by a motor position sensor.

In some embodiments, controller 402 is configured to operate the control the motors 400 through user engagement of the user interface and/or through programming instructions. FIG. 5 illustrates an embodiment in which a position sensor 508 is operably engaged with a motor 500 and/or a controller 502. A motor switch 504 such as any of the motor switches described herein can be operated according to principles discussed above to electrically couple the controller 502 to one or more batteries 506. A position sensor 508, such as but not limited to a Hall sensor or any other sensor described herein or known in the art, outputs a signal representative of a position of the motor 500 or any other part of the arm assembly or needle and sends the signal to the controller 502. Using the position sensor 508, the controller 502 can operably control the motor 500 to locate or rotate the needle as needed to achieve a desired result.

Figure 6:
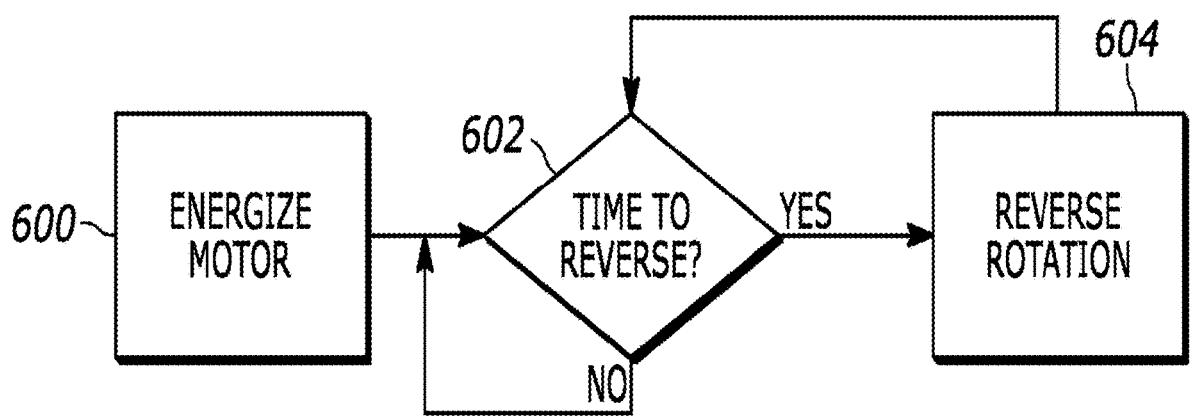
FIG. 6 is a flow chart of logic implemented by the circuit of FIG. 4.

FIG. 6 illustrates logic embodied in or communicable with the controller 402, 502. Commencing at state 600, the motor is energized. When a time period is determined to have elapsed at state 602, the direction of rotation of the rotor of the motor is reversed at state 604. The logic loops back to state 602 to continue to reverse the direction of rotation at various time periods, which may be predetermined in some embodiments, until the motor is deenergized, to cause the motor to oscillate during energization.

Figure 7:
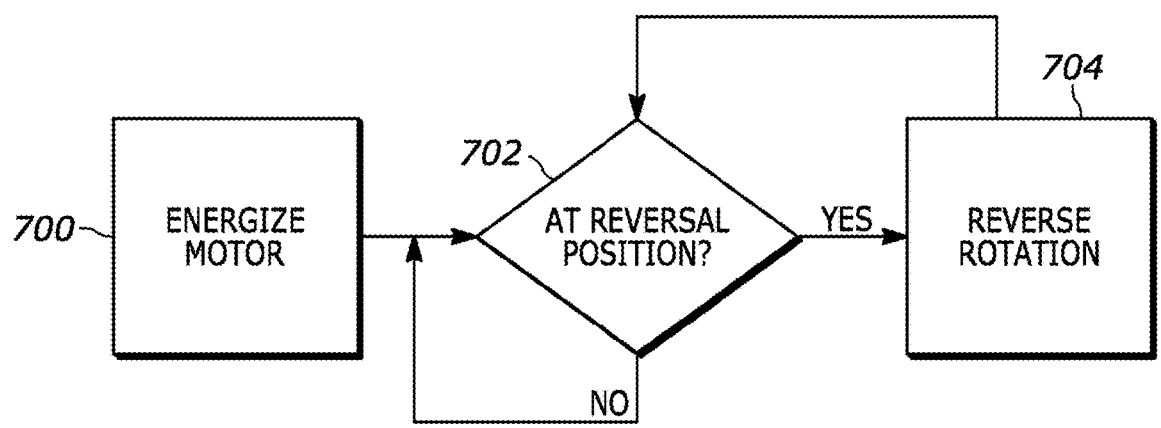
FIG. 7 is a flow chart of logic implemented by the circuit of FIG. 5.

When a position sensor 508 is implemented as shown in FIG. 5, the logic of FIG. 7 may be employed by the controller. The motor is energized at block 700, and upon determination at state 702 based on the signal from the position sensor that a position of the motor has been attained, the direction of rotation of the motor is reversed at state 704. Note that the position at which rotation is reversed may be multiples of a particular angle so that the motor is reversed after one or multiple rotations. For example, the rotor position for reversal may be at 0 degrees, 720 degrees (two full rotations), then again at 1440 degrees (after another two full rotations), etc. Alternatively, the rotor position for reversal may be every 180 degrees, i.e., less than a complete rotor rotation. The logic loops back from state 704 to state 702 to continue to reverse the direction of rotation until the motor is deenergized to cause the motor to oscillate during energization.

Figure 8:
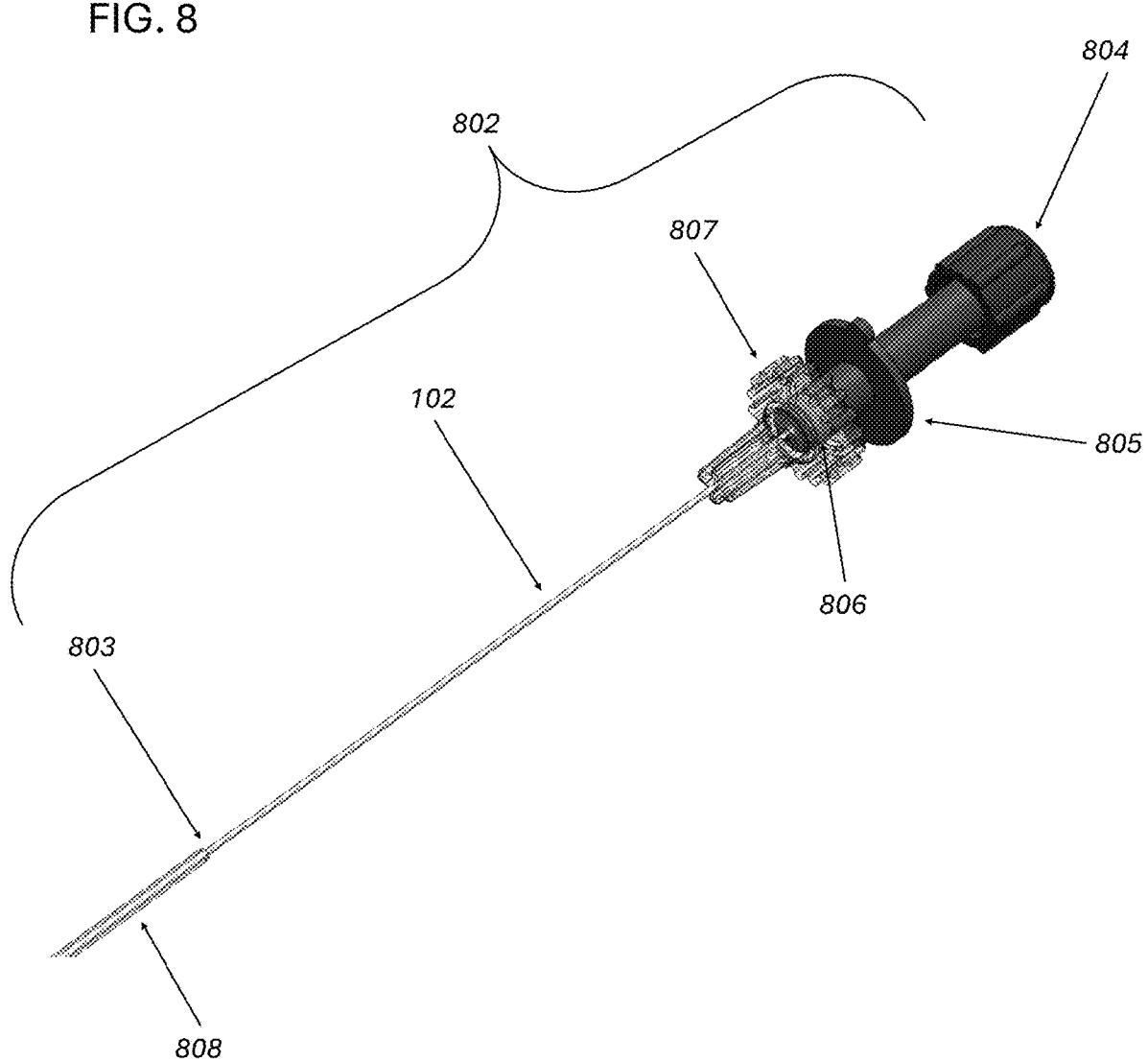
FIG. 8 is a perspective view of the needle assembly.

Referring now to FIG. 8, the present invention may employ a needle assembly 802 including an elongated needle 102 with a sharp cutting edge 803 to facilitate cutting tissue when the needle 102 is advanced into tissue and rotated. The needle 102 may be a hollow metal hypodermic needle of a size of between 18 to 27 gauge, and more particularly 22-25 gauge with a cutting edge 803, and with a length of 1200 mm to 1300 mm. The cutting edge 803 may include bevels, serrations, or other geometries to optimize its ability to cut through biological material during oscillatory or translational motion.

The needle assembly 802 may be entirely disposable, including the needle 102, a stylet 804, a luer hub 805, and an O-ring 806-packaged in sterile, single-use kits. The needle 102 itself is constructed from medical-grade stainless steel or titanium to ensure strength, durability, and biocompatibility. In an alternate embodiment, the components may be reusable and constructed from autoclavable materials suitable for repeated use.

The needle assembly 802 further includes a needle gear 807 having gear teeth disposed around the needle gear 807. In some embodiments, the needle gear 807 could be detachable from the luer hub 805. The gear teeth are configured to meshingly engage the gear wheel 132 that protrudes from the needle translator 130. As a result, the motor supported in the needle translator 130 rotates the geared wheel 132 which rotates the needle 102. The needle 102 has the capacity for rotational speeds between sixty (60) revolutions per minute (RPM) to three hundred fifty (350) RPM, inclusive.

The O-ring 806 of the needle assembly 802 surrounds the portion of the luer hub 805 that sits within the interior of the geared wheel 807. The connection of the geared wheel 807 to the luer hub 805 is a friction or press fit connection facilitated by an O-ring 806. The luer hub 805 is constructed with a groove to receive the O-ring 806 and maintain its position. This configuration allows the luer hub 805 to remain static while the geared wheel 807 and needle 102 rotate to maintain an airtight seal between the geared wheel 807 and the luer hub 805.

The hollow interior of the needle 102 establishes a collection chamber. In an alternative embodiment, the collection chamber includes a separate, removable tissue chamber, which can be detached for direct sample retrieval without disassembling the entire system. A continuous fluid passageway is formed by the hollow interior through the removable distal hub, removable proximal hub, and luer hub. In an embodiment, the needle assembly 802 includes a valve, such as but not limited to a slide valve or stopcock, to lock vacuum in the tissue chamber and occlude tissue from entering the suction tubing. The valve can be embedded within the cylinder supporting the luer hub 805 and O-ring 806.

A stylet 804 is secured to the proximal end of the needle assembly 802, opposite the cutting edge 803. The stylet 804 is a thin, solid wire inserted inside the needle 102 to maintain the needle's rigidity and prevent tissue from obstructing the tissue chamber during insertion. Once the device is assembled, the stylet 804 is removed and the suction tubing 109 is attached.

Finally, the needle assembly 802 includes a sheath 808 that surrounds the needle 102, providing additional stability and ensuring safe handling and operation during medical procedures. The sheath 808 is constructed from biocompatible materials, such as but not limited to medical-grade stainless steel or autoclavable polymers, designed to withstand high-speed oscillatory forces and axial translation while maintaining structural integrity.

Figure 9:
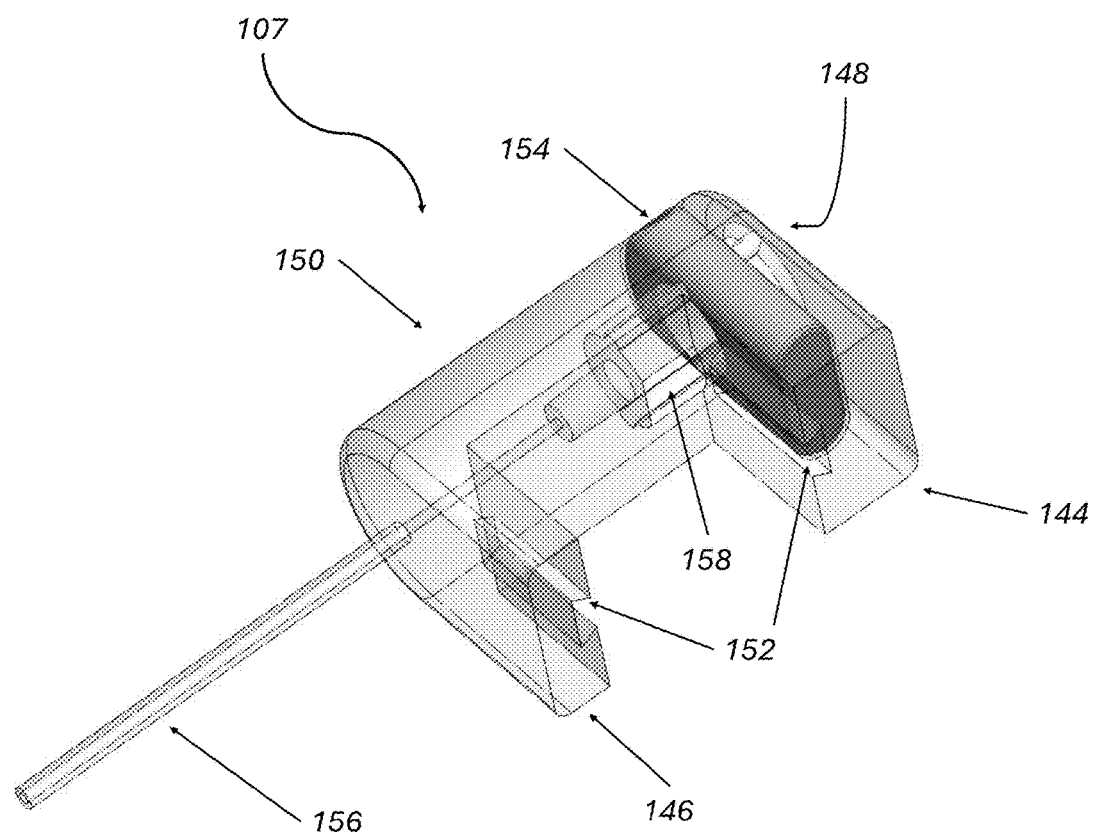
FIG. 9 is an x-ray view of the proximal hub.

Referring now to FIG. 9 proximal hub 107 may be removably coupled to the needle translator 130 to securely hold the needle 102 and integrate with the needle translator 130 and gear 132. In an embodiment, the proximal hub 107 may be is a semi-rounded cylinder with at least one of an upper portion 144 and a lower portion 146 having associated widths and extending horizontally toward the needle translator 130. The upper portion 144 and lower portion 146 function to removably attach the proximal hub 107 to the needle translator 130. The upper portion 144 includes a central opening 148 configured to receive the needle assembly 802. The outer casing 150 of the proximal hub is constructed from medical-grade stainless steel or autoclavable high-performance polymers, such as PEEK, to withstand sterilization cycles and ensure a long operational life. In disposable embodiments, the hub may be made from lightweight polycarbonate for single-use applications in sterile environments. Its internal surfaces are designed with smooth contours to prevent material buildup and facilitate cleaning, while external components include minimal sharp edges to reduce the risk of accidental contamination during handling.

The upper portion 144 and lower portion 146 include an attachment mechanism 152, such as but not limited to dovetail guides, to facilitate secure, removable attachment to the needle translator 130. The attachment mechanism 152 allows the proximal hub 107 to slide into position along matching channels on the needle translator 130, locking it firmly in place to prevent any lateral or rotational movement during operation. In another embodiment, the attachment mechanism 152 includes but is not limited to keyed slots or magnetic couplings to securely fit the removable proximal hub 107 to the needle translator 130. However, it is contemplated that alternative attachment mechanisms can be used.

The upper portion 144 includes an internal luer hub retention latch 154 configured to receive the luer hub 805 of the needle assembly 802. The retention latch 154 includes a through-hole in line with the central opening 148 of the proximal hub 107, which allows the needle assembly 802 to fit inside the proximal hub 107. The through-hole has a diameter sufficient to securely insert the needle gear 807. The locking mechanism of the retention latch 154 may include but is not limited to a spring-loaded clamp, friction, snap-fit, or any alternative design to easily insert and remove the needle assembly. The retention latch 154 may be constructed from durable materials capable of repeated sterilization such as but not limited to stainless steel, titanium, or high-strength polymers like PEEK.

To maintain a sterile and airtight seal, the latch 154 is configured to engage with the O-ring 806 at the interface with the luer hub 805. The O-ring 806 ensures no vacuum leaks occur during operation, preserving the integrity of the vacuum system.

An anti-buckling tube 156 attached to the distal end of the proximal hub 107 ensures the stability and proper axial alignment of the needle assembly 802 during operation. The anti-buckling tube 156 is constructed from durable materials with an ability to withstand repeated sterilization cycles. The inner surface of the tube 156 is polished or coated with a low-friction material, such as but not limited to PTFE (Teflon), to minimize resistance as the needle 102 moves axially or oscillates within the tube 156. This surface treatment also prevents the buildup of biological debris or contaminants during operation, facilitating cleaning and maintenance.

The anti-buckling tube 156 is hollow and cylindrical, with an inner diameter slightly larger than the needle's 102 outer diameter. This tight clearance ensures that the needle 102 is fully supported while allowing for unimpeded axial translation and oscillation. The length of the tube 156 is calibrated to match the distance between the proximal hub 107 and the distal hub 108. This length prevents buckling across the entire unsupported span of the needle 102.

Internally, the proximal hub 107 includes a receiver 158 that is configured to receive to the needle gear 807. The receiver 158 secures the needle assembly 802 and allows the needle gear 807 to be in mechanical communication with the gear 132 of the needle translator 130. The receiver 158 aligns with corresponding needle gear 807 in the needle assembly 802. The receiver 158 may be constructed from materials such as but not limited to hardened stainless steel or high-strength alloys, chosen for their durability and resistance to wear under repeated high-frequency operation. The internal surfaces of the receiver 158 may be coated with low-friction materials, such as but not limited to PTFE (Teflon) or ceramic composites, to enhance efficiency and minimize heat generation during prolonged use.

Figure 10:
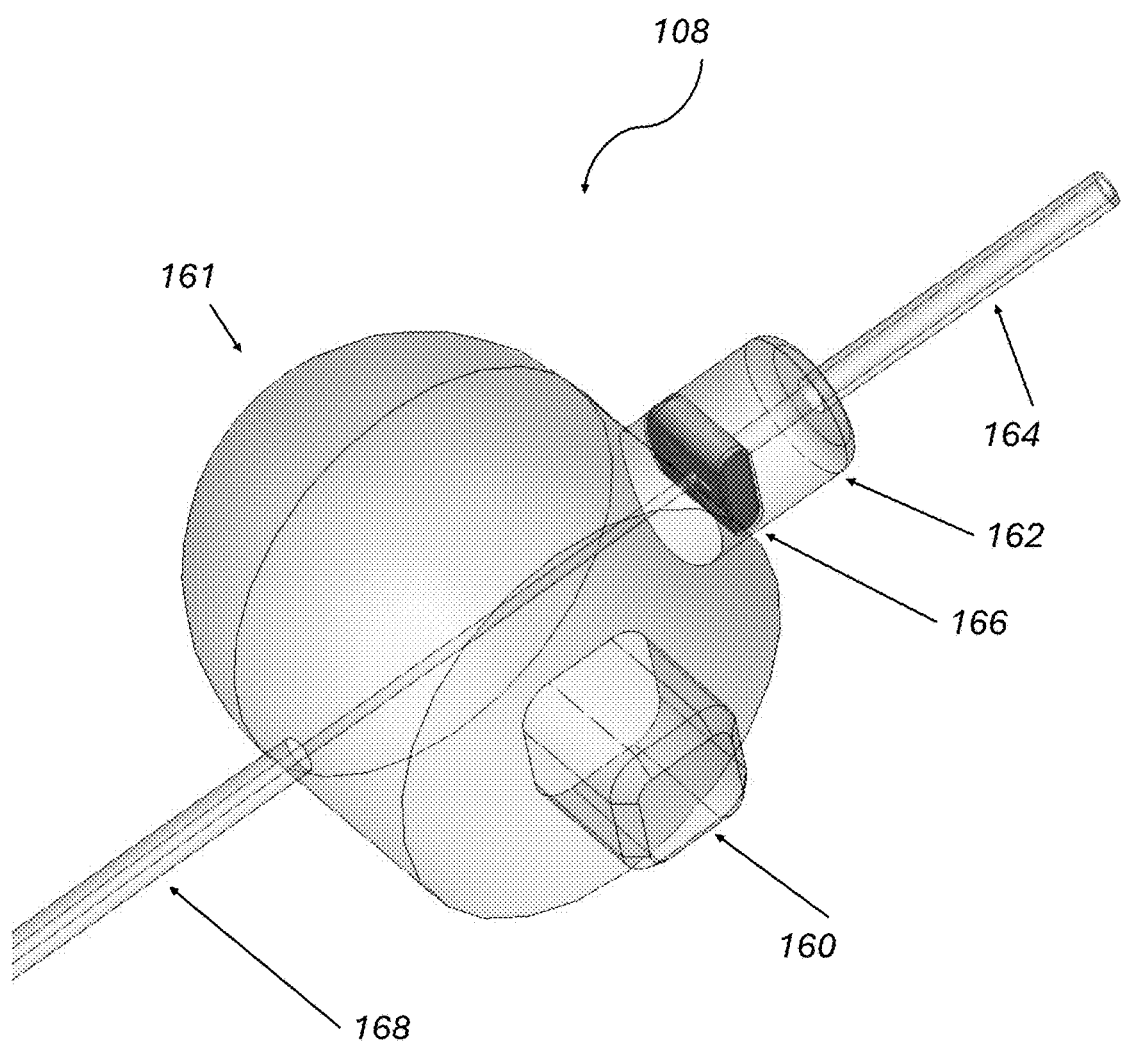
FIG. 10 is an x-ray view of the distal hub.

FIG. 10 shows a removable distal hub 108 mechanically connected to the terminal joint 126 on the robot arm assembly 106 that is configured to secure, guide, and stabilize the needle 102 during a medical procedure. In one embodiment, the distal hub 108 includes a securing mechanism 160, such as but not limited to a keyed mating system. This securing mechanism 160 uses alignment features, such as but not limited to dovetail slots or bayonet-style connectors, to ensure secure and repeatable attachment to the arm assembly 106. The securing mechanism 160 may include spring-loaded pins or locking tabs to provide quick-release functionality, enabling operators to detach or reattach the hub without requiring specialized tools.

The outer case 161 of the distal hub 108 may be a low-profile, smoothed surface to protect internal components, ease cleaning, and avoid damage or unwanted contact with the environment that could interrupt medical procedures. The outer casing 161 may be constructed from medical-grade materials, such as but not limited to anodized aluminum, stainless steel, or high-performance polymers like PEEK, ensuring durability under repeated use and compatibility with autoclave sterilization cycles. In another embodiment, the distal hub 108 is disposable.

An extended portion 162 of the distal hub 108 extends proximally toward the needle 102 and is attached to a guide tube 164. The guide tube 164 is configured to have a slightly larger diameter than the anti-buckling tube 156 extending from the lower extended portion 162 of the removable proximal hub 107. Once assembled, the anti-buckling tube 156 is positioned with the free end sitting inside of the free end of the guide tube 164.

The guide tube 164 is constructed from high-strength, low-friction materials such as but not limited to polished stainless steel, PTFE (polytetrafluoroethylene), or ceramic-coated alloys, to withstand repeated rounds of sterilization and maintain performance over extended use. In one embodiment, the guide tube 164 and proximally extended portion 162 of the distal hub 108 comprise a singular, contiguous element of the device 101. In another embodiment, the guide tube 164 is independent from the distal hub 108 and is attached via a secure and vibration resistant connection, such as but not limited to a threaded connection, press-fit collar, or locking clamp. In an embodiment, the guide tube 164 may also include an integrated sealing system, such as but not limited to rings or gaskets, at the junctions where it interfaces with the distal hub 108 and anti-buckling tube 156.

A sheath clamping latch 166 is internally integrated into the proximally extended portion 162 of the distal hub 108, positioned perpendicularly to the vertical axis of the extended portion 162. An opening in the center of the sheath clamping latch 166 is oriented to receive and secure the sheath 808 surrounding the needle 102 and allow the needle 102 to pass through the distal hub 108. The clamping latch 166 may include but is not limited to a sliding collar, twist-lock mechanism, or spring clamp to hold the sheath firmly in place during operation while allowing for easy removal when replacing the sheath.

The clamping latch 166 is constructed from autoclavable materials, such as but not limited to anodized aluminum, stainless steel, or high-strength polymers like PEEK, to ensure durability and compatibility with repeated sterilization cycles. For disposable embodiments, the latch can be made from medical-grade plastics, such as polycarbonate or polypropylene, offering cost-efficient single-use solutions. In some embodiments, the clamping latch 166 includes an adjustable locking system to accommodate sheaths of varying diameters or lengths.

An endoscope 168 integrated into the removable distal hub 108, positioned opposite the guide tube 164, and provides real-time visual feedback during medical procedures. The endoscope 168 is housed within a dedicated channel or sleeve inside the distal hub 108, running parallel to the needle assembly 802. The endoscope 168 includes an optical system, such as but not limited to a miniature camera module or fiber optic bundle at the distal end, designed to capture high-resolution images or videos. In an embodiment, the endoscope 168 may include features such as zoom functionality, autofocus, or panoramic views, depending on the procedural requirements.

Figure 11:
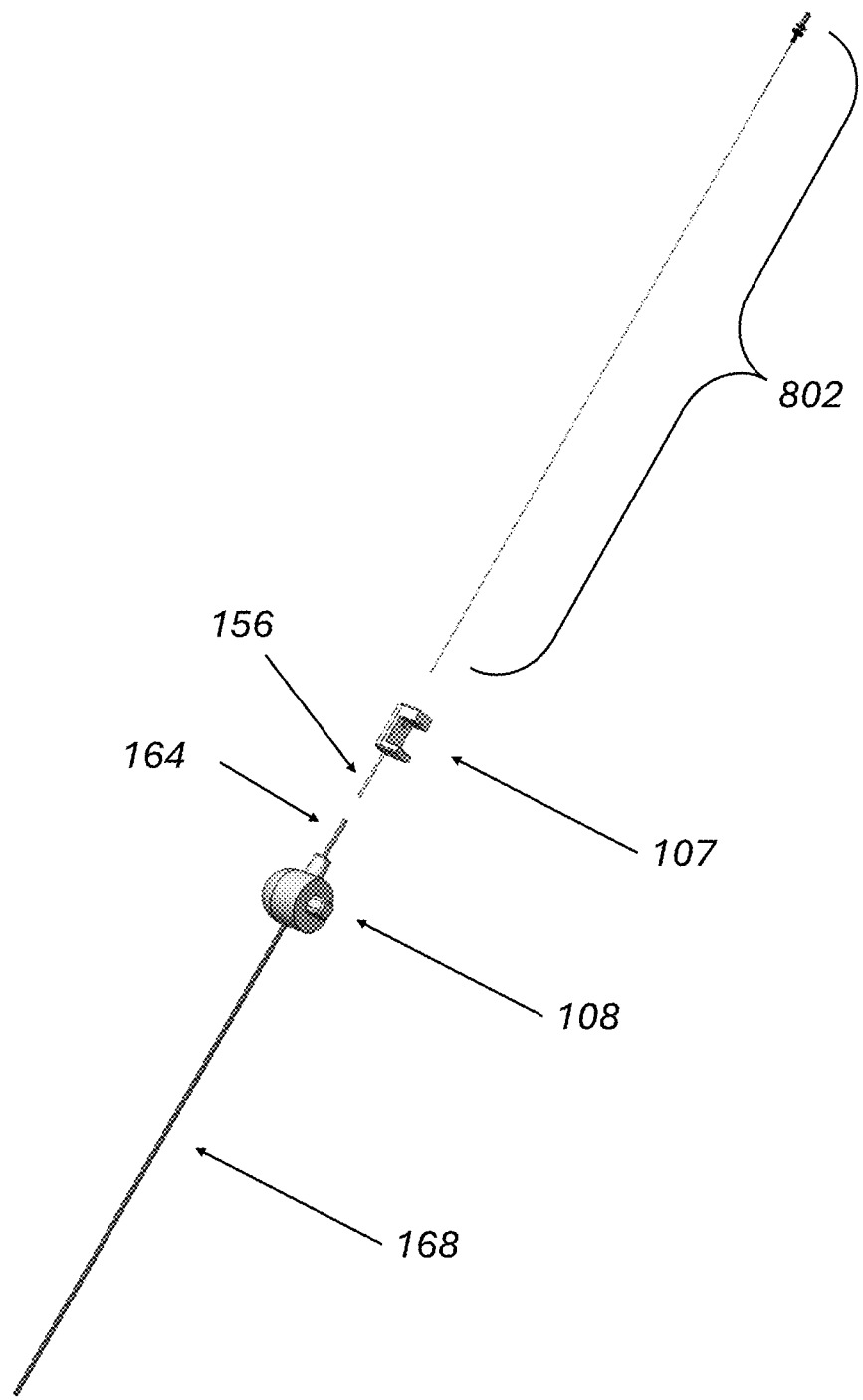
FIG. 11 is an exploded view of the needle assembly, proximal hub, and distal hub.

FIG. 11 shows an exploded view of the needle assembly 802, proximal hub 107, and distal hub 108 prior to assembly. To assemble the overall device 101, the needle assembly 802 is inserted into the proximal hub 107 so that the needle assembly 802 passes through to the anti-buckling tube 156 of the proximal hub 107. The anti-buckling tube 156 is inserted into the guide tube 164, creating a continuous passage for the needle assembly 802 from the proximal hub 107 to the endoscope 168. The proximal hub 107 and distal hub 108 are then loaded onto the robotic arm assembly 106 prior to operation, as shown in FIG. 12.

Figure 12:
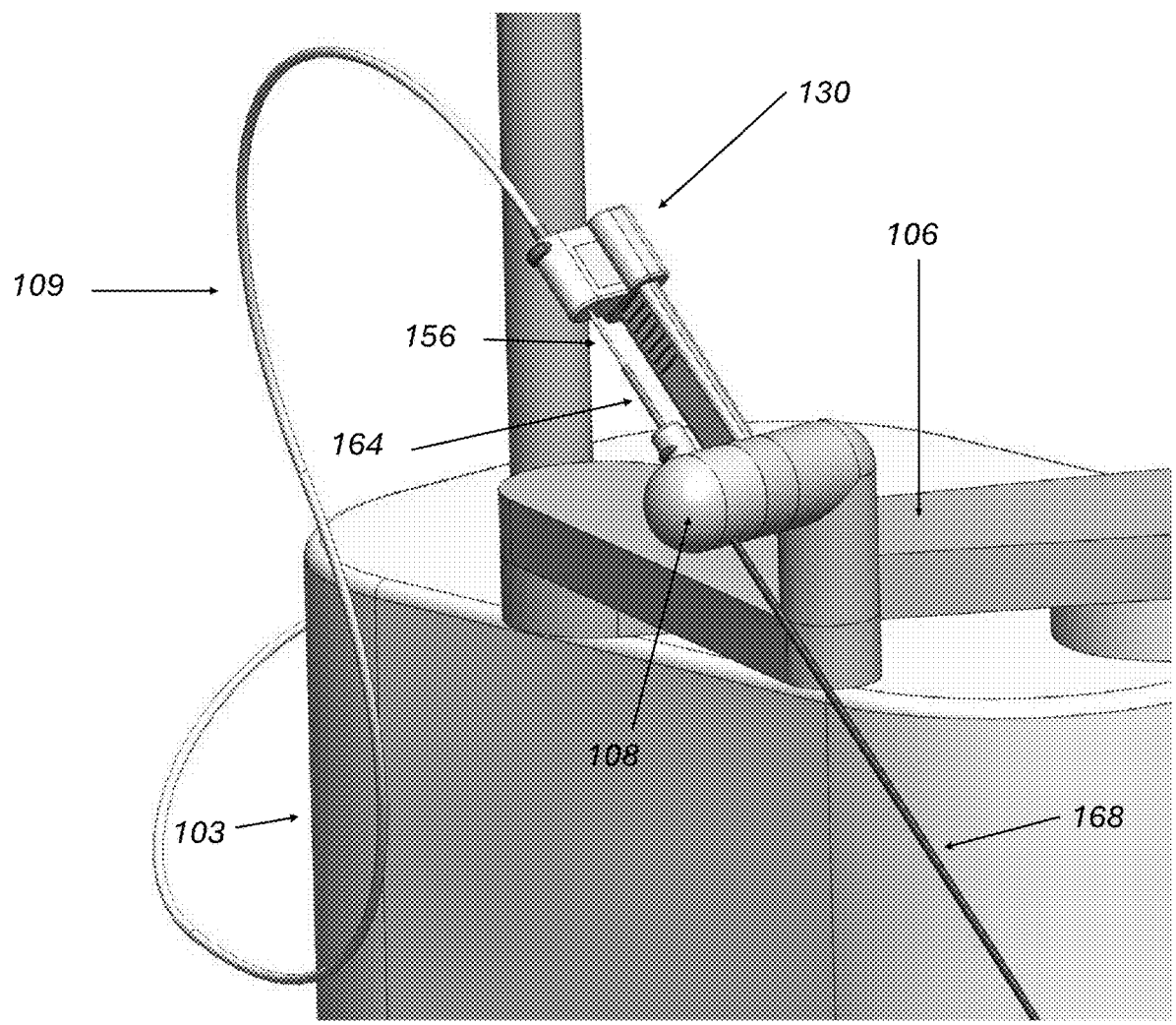
FIG. 12 is a perspective view robot arm as assembled prior to operation.

Continuing the description for FIG. 12, suction tubing 109 connects distally to the needle assembly 802 and proximally to the main body 103. The tubing 109 is constructed from medical-grade materials such as but not limited to silicone, thermoplastic elastomers (TPE), or other suitable material, chosen for their biocompatibility, flexibility, and resistance to wear and tear. The tubing 109 construction includes an inner layer for maintaining suction flow integrity and an outer layer for mechanical protection.

The tubing 109 is typically manufactured in lengths of 1 to 3 meters, with an inner diameter ranging from 3 to 5 millimeters to balance suction efficiency and flexibility. For applications requiring higher suction rates, larger diameters may be used, while smaller diameters are preferred for more delicate procedures. In another embodiment, reinforced versions of the tubing 109 may include an outer metal wire helix or ribbing to prevent kinking or collapse under vacuum pressure, ensuring consistent suction performance during operation. This reinforcement also enhances resilience when bent or compressed within the robotic arm's constrained pathways.

Figure 13:
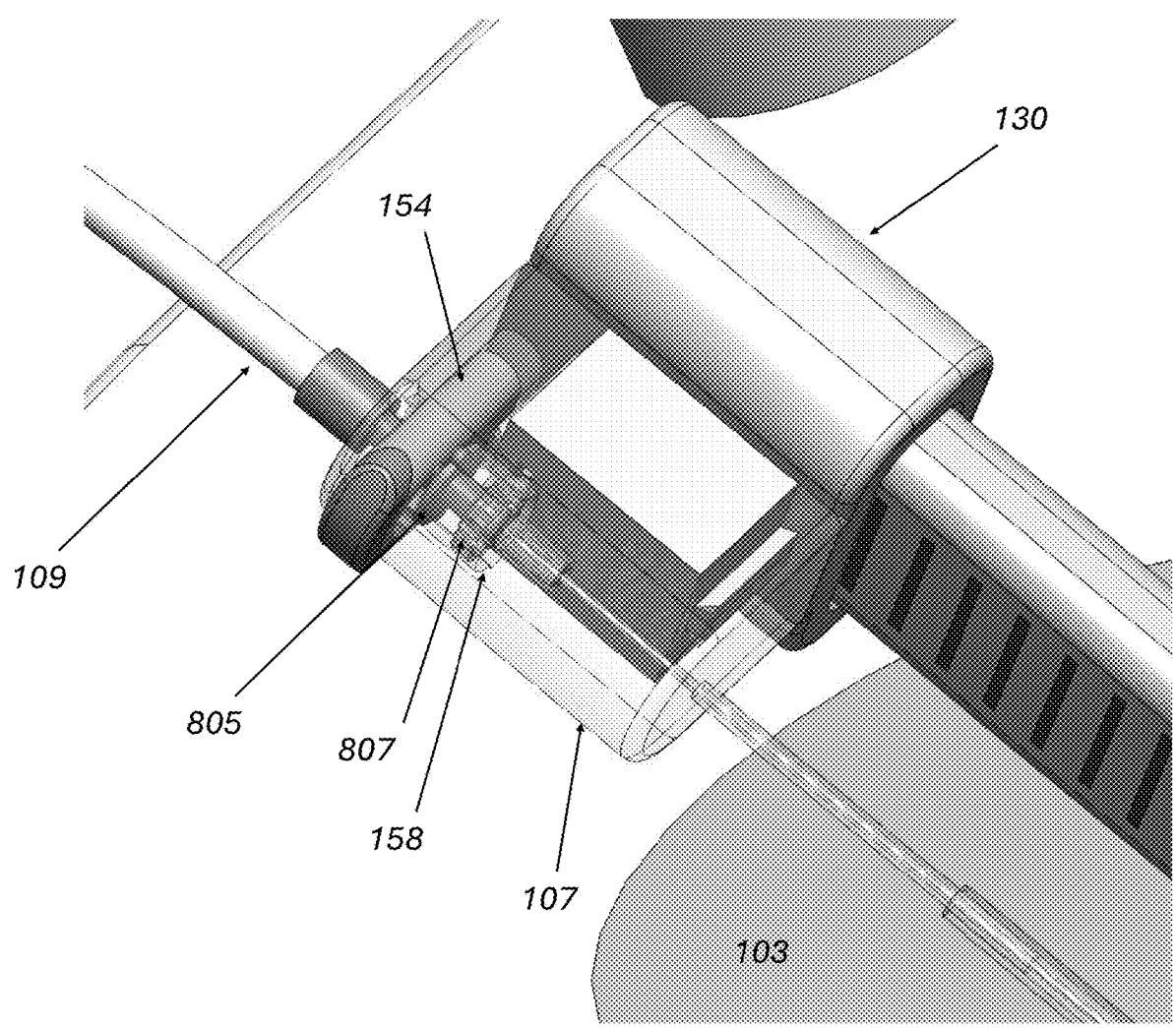
FIG. 13 is an x-ray view of the proximal hub coupled to the housing unit with the needle assembly and suction tubing in place.

FIG. 13 shows an x-ray view of the proximal hub 107 attached to the needle translator 130. In the configuration shown, the needle gear 807 is secured in the receiver 158 of the proximal hub 107. The luer hub retention latch 154 engages the luer hub 805 to secure the needle assembly 802. The distal end of the suction tubing 109 is connected to the proximal end of the needle assembly 802 where the stylet 804 was attached prior to overall assembly of the device 101.

The proximal end of the tubing 109 attaches to the main body 103 through a quick-connect/disconnect coupling system that facilitates rapid assembly and disassembly without requiring specialized tools. In an embodiment, this coupling to the main body 103 may incorporate a one-way valve, which automatically seals when the tubing 109 is detached, preserving system pressure and preventing contamination.

In an embodiment, the suction tubing 109 is configured to be disposable and provided in sterile packaging to ensure contamination-free use in medical procedures. The disposable suction tubing 109 connects to the main body 103 and the needle assembly 802 through reusable hardware designed for secure, sterile, and easy-to-clean operation. Mechanisms connecting the suction tubing 109 to the device 101 are constructed to withstand repeated sterilization cycles, with smooth, non-porous surfaces to facilitate thorough cleaning and prevent the buildup of contaminants.

Figure 14:
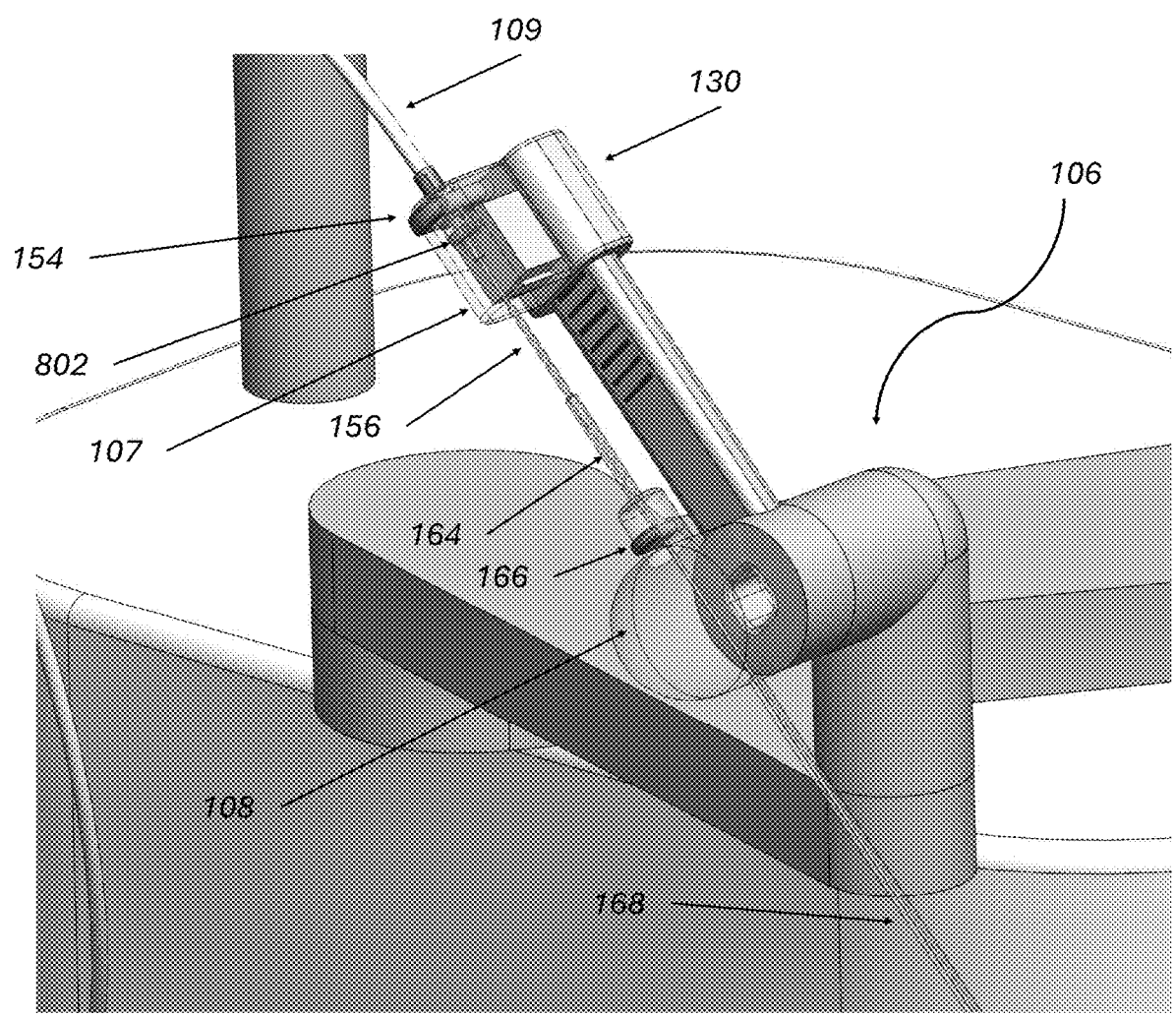
FIG. 14 is an x-ray view of the robot arm as assembled prior to operation.
Figure 15:
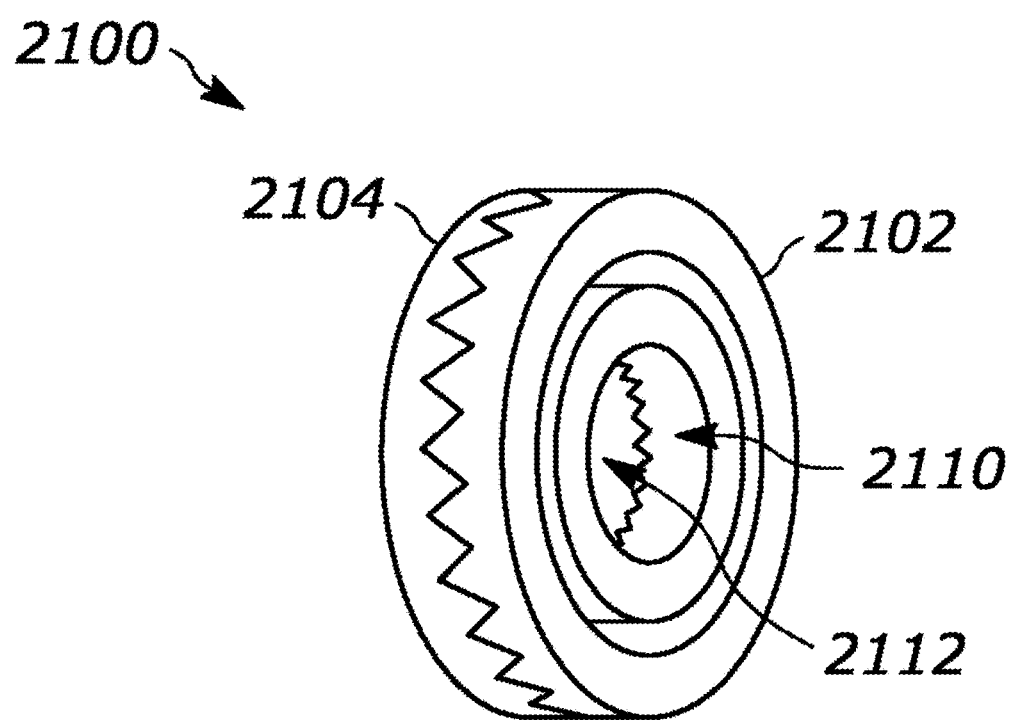
FIG. 15 depicts an embodiment of a gear assembly for an axial oscillation mechanism for the needle.
Figure 16:
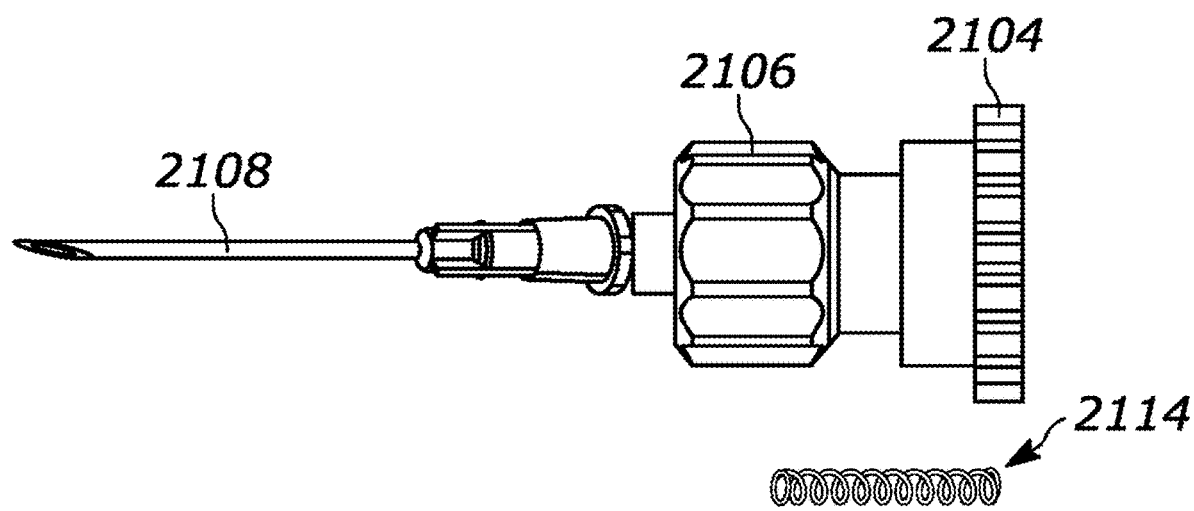
FIG. 16 depicts a partial exploded view of an embodiment of an axial oscillation mechanism and the needle.
Figure 17:
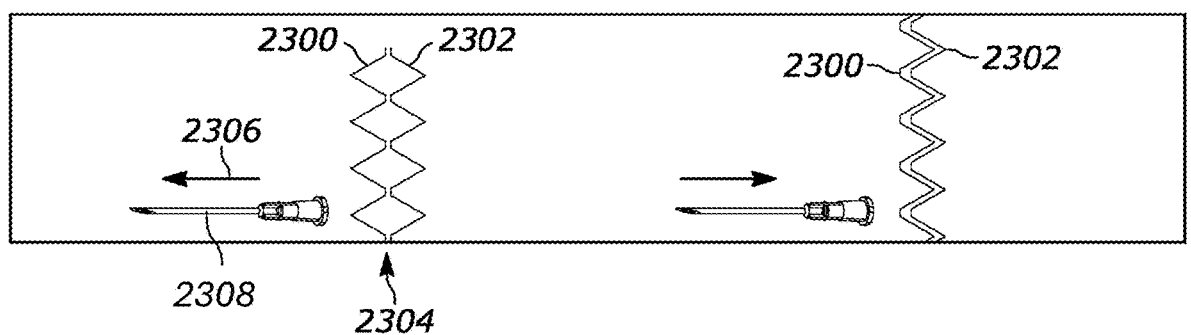
FIG. 17 is a diagram illustrating the axial oscillation of the needle as the gear assembly rotates.
Figure 18:
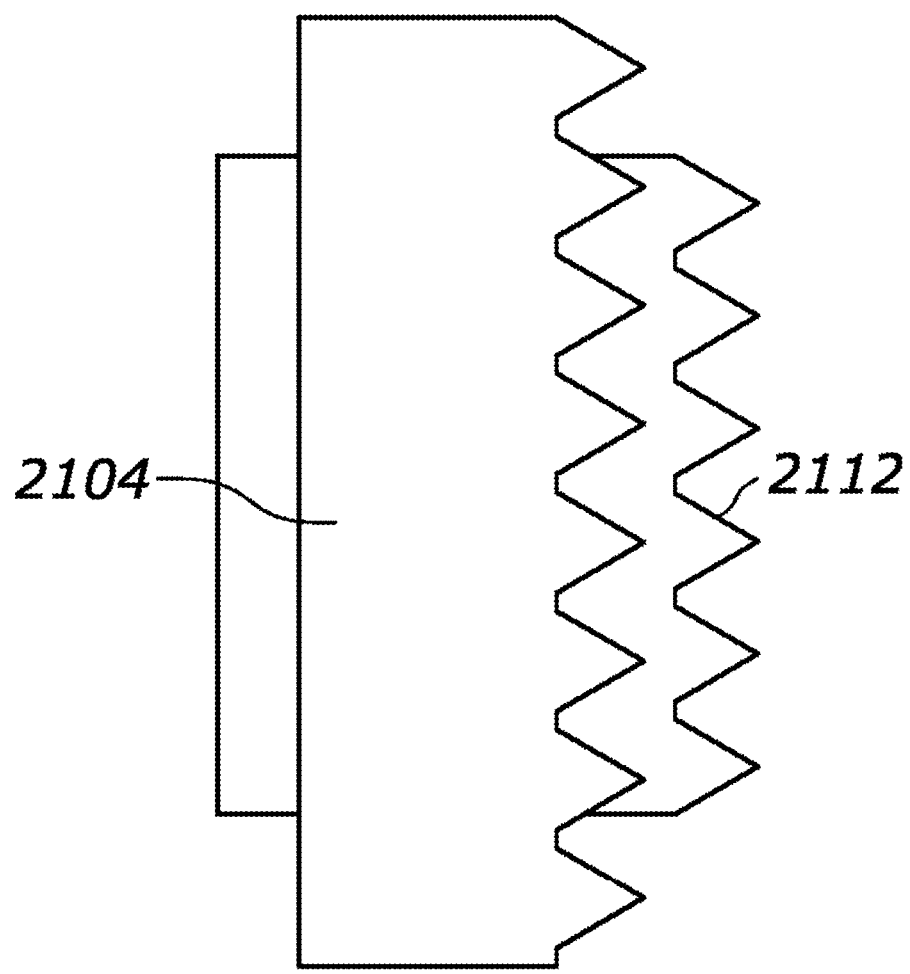
FIG. 18 depicts an embodiment of a gear assembly for an axial oscillation mechanism for the needle.
Figure 19:
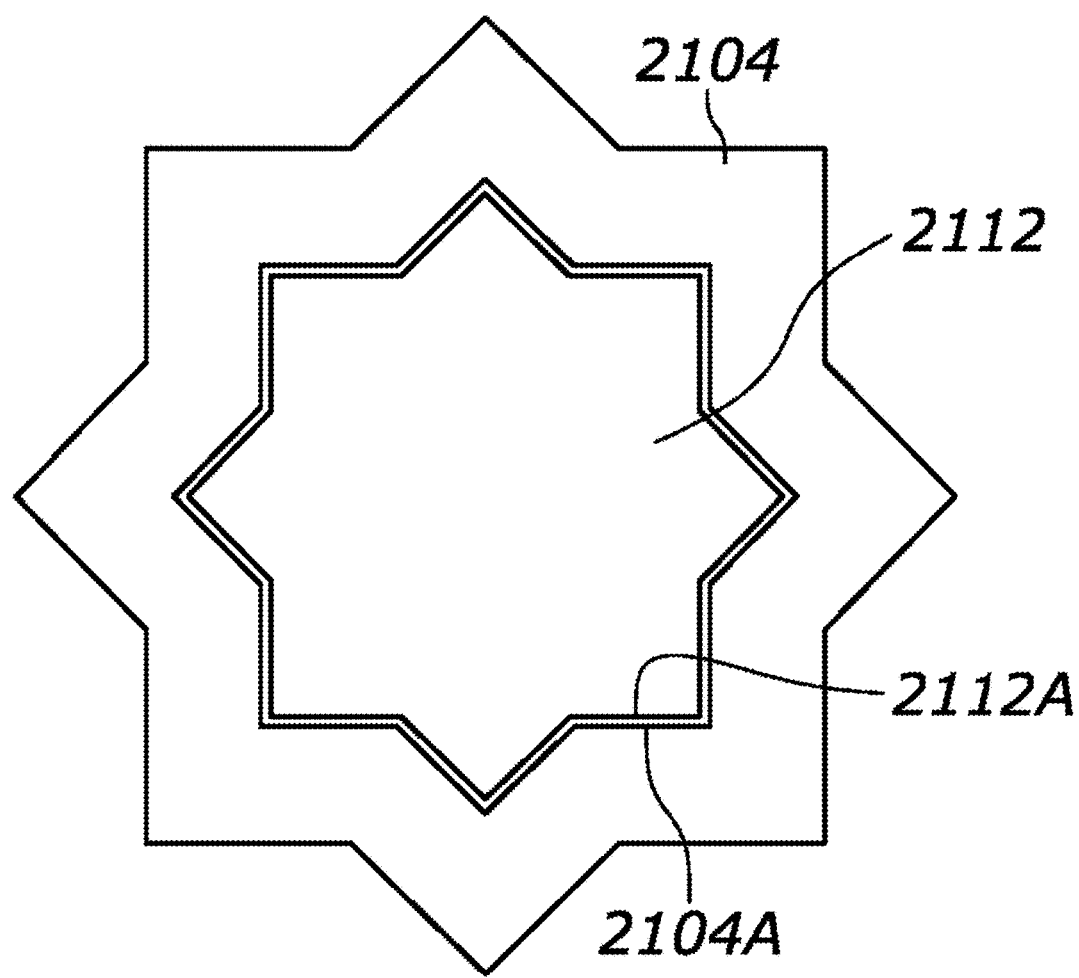
FIG. 19 depicts an embodiment of a gear assembly for an axial oscillation mechanism for the needle.
Figure 20:
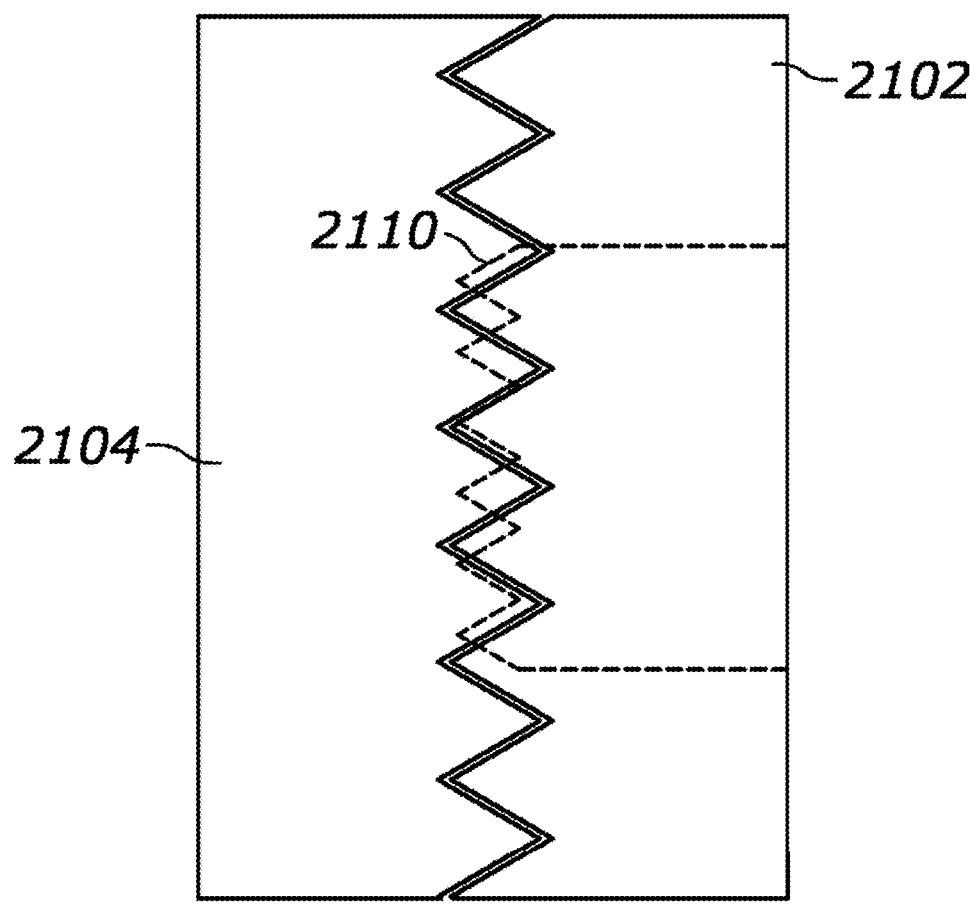
FIG. 20 depicts an embodiment of a gear assembly for an axial oscillation mechanism for the needle.
Figure 21:
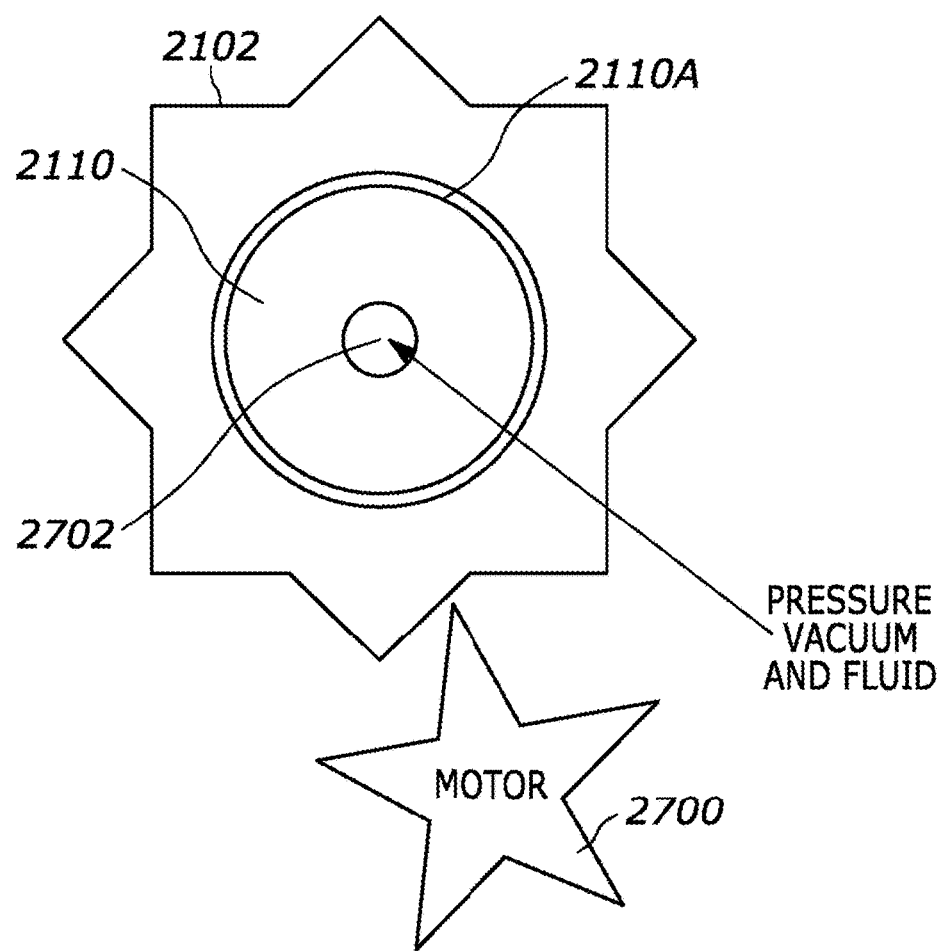
FIG. 21 illustrates an axial oscillation mechanism for the needle.

FIG. 14 shows a complete x-ray view of the distal portion of the robot arm assembly 106 connected to the proximal hub 107 and distal hub 108. The needle assembly 802 is secured by the luer hub retention latch 154 in the proximal hub 107, which in turn is connected to the needle translator 130. The distal end of the suction tubing 109 is connected to the proximal end of the needle assembly 802, as previously described. The anti-buckling tube 156 is positioned with its distal end sitting within the diameter of the proximal end of the guide tube 164. The sheath clamping latch 154 is engaged to secure the sheath 808 and allow the needle assembly 802 to pass through the distal hub 108 to the endoscope 168.

The device 101 can be configured to employ various microcontrollers (MCUs) and processors. In one embodiment, low to mid-range MCUs like the Arduino family (e.g., ATmega328, ATmega2560) are suitable due to their low power consumption and straightforward programming. More sophisticated configurations may require advanced MCUs, such as the STM32, that offer advanced peripherals like timers, ADCs, and communication interfaces (CAN, PC, SPI). These are ideal for subsystems that manage real-time data from multiple sensors or control robotic arms. Higher-performance MCUs, such as the Texas Instruments Tiva C series or ESP32, can handle more complex operations like multi-axis motor synchronization and wireless communication through integrated Wi-Fi and Bluetooth. For tasks such as real-time video processing or advanced user interfaces, single-board computers (SBCs) like the Raspberry Pi (4B, CM4) or NVIDIA Jetson Nano/Xavier are highly effective. These processors are capable of handling machine learning and computer vision, making them suitable for systems requiring AI-driven decision-making. Industrial-grade processors, including Intel Core i3/i5 or AMD Ryzen Embedded, provide powerful multi-threading capabilities for teleoperation and real-time data streaming. Additionally, field-programmable gate arrays (FPGAs), such as the Xilinx Zynq or Intel Cyclone series, offer custom hardware acceleration for tasks requiring ultra-fast response times, such as fine needle positioning or high-frequency oscillation control.

The software architecture is built on a combination of microcontroller and single-board computer (SBC) environments. For microcontrollers, development can be carried out using Arduino IDE or PlatformIO, allowing for efficient coding of low-level operations such as motor control and sensor data acquisition. SBCs, such as Raspberry Pi or NVIDIA Jetson, handle higher-level tasks and are programmed in Python, C++, or other comparable languages. These environments can integrate specialized libraries like OpenCV for computer vision, enabling advanced features such as image processing and object tracking. The system's modular software design ensures scalability, allowing new functionalities to be added as needed.

The techniques introduced here can be embodied as special-purpose hardware (e.g. circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compacts disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

A computer readable signal medium may include a propagated data signal with computer readable program PIN embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program PIN embodied on a computer readable medium may be transmitted using any appropriate medium, including but not limited to wireless, wire-line, optical fiber cable, radio frequency, etc., or any suitable combination of the foregoing. Computer program PIN for carrying out operations for aspects of the present invention may be written in any combination of one or more programming languages, including an object oriented programming language such as Java, C#, C++, Python, MATLAB, and/or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computing device, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

What is claimed is:

1. A robotic medical device, comprising:
    a needle assembly, the needle assembly including:
        a hollow needle;
        a needle gear at a proximal end of the hollow needle;
        a luer hub with an O-ring, wherein the needle is configured to rotate relative to the luer hub;
    a robotic arm, the robotic arm including:
        multiple joints providing at least three degrees of freedom;
        a translation guide and a needle translator configured to axially translate the needle assembly about a length of the translation guide;
        a motor configured to operably engage the needle gear and thereby rotate the needle about a longitudinal axis of the needle;
    a tissue chamber being established at least in part by a hollow interior of the needle and in fluidic communication with a vacuum source via a suction tube;
    a proximal hub configured to house the proximal end of the needle and temporarily attach to the needle translator;
    a distal hub configured to be temporarily coupled to the robotic arm at a distal location relative to the proximal hub;
    wherein the needle translator is configured to axially translate the proximal hub and needle relative to the distal hub and rotate the needle about the longitudinal axis of the needle and the tissue chamber is subject to the vacuum.

2. The device of claim 1, wherein the proximal hub comprises:
    a removable attachment mechanism;
    a luer hub retention latch;
    an interface for transferring rotational motion from the motor to the needle gear; and
    an anti-buckling tube extending towards the distal hub, wherein the needle passes through the anti-buckling tube.

3. The device of claim 1, wherein the distal hub comprises:
    a removable attachment mechanism;
    a sheath clamping latch;
    a guide tube; and
    an endoscope.

4. The device of claim 1, wherein the needle assembly and suction tube are disposable.

5. The device of claim 1, wherein the robotic arm includes a detachable joint mechanism with alignment pins and a quick-release locking collar to facilitate removal and reattachment.

6. The device of claim 1, further comprising sensors, including:

a position sensor configured to monitor movement of the robotic arm;

a pressure sensor configured to monitor vacuum levels within the tissue chamber; and a force-torque feedback sensor configured to monitor the rotation and translation of the needle.

7. A robotic medical device, comprising:
a needle assembly, the needle assembly including:
a hollow needle;
a needle gear disposed proximate to a proximal end of the hollow needle;
a luer hub with an O-ring, wherein the needle is configured to rotate relative to the luer hub;
a robotic arm, the robotic arm including:
a translation guide and a needle translator configured to axially translate the needle assembly about a length of the translation guide;
a proximal hub configured to house the needle and temporarily attach to the needle translator;
a motor configured to operably engage the needle gear and thereby rotate the needle about a longitudinal axis of the needle;
a distal hub configured to be temporarily coupled to a terminal joint of the robotic arm, wherein the distal hub includes a passage for receiving the needle;
a tissue chamber being established at least in part by a hollow interior of the needle and in fluidic communication with a vacuum source via a suction tube;
wherein the needle translator is configured to axially translate the proximal hub and needle relative to the distal hub while the needle is rotated relative to the longitudinal axis of the needle and the tissue chamber is subject to a vacuum.

8. The device of claim 7, wherein the proximal hub comprises:
a removable attachment mechanism;
a luer hub retention latch; and
an interface for transferring rotational motion from the motor to the needle gear.

9. The device of claim 7, further including an anti-buckling tube extending at least partially between the distal hub and the proximal hub through which the needle passes, wherein the anti-buckling tube has greater rigidity than the needle.

10. The device of claim 7, wherein the distal hub comprises:
a removable attachment mechanism;
a sheath clamping latch;
a guide tube; and
an endoscope.

11. The device of claim 7, wherein the needle assembly and suction tube are disposable.

12. The device of claim 7, wherein the robotic arm includes a detachable joint mechanism with alignment pins and a quick-release locking collar to facilitate removal and reattachment.

13. The device of claim 7, further comprising sensors, including:

a position sensor configured to monitor movement of the robotic arm;

a pressure sensor configured to monitor vacuum levels within the tissue chamber; and a force-torque feedback sensor configured to monitor the rotation and translation of the needle.

14. A robotic medical device, comprising:
a needle assembly, the needle assembly including:
a hollow needle;
a needle gear disposed proximate to a proximal end of the hollow needle;
a robotic arm, the robotic arm including:
a translation guide and a needle translator;
a proximal hub configured to house the proximal end of the needle and temporarily attach to the needle translator;
a motor configured to operably engage the needle gear and thereby rotate the needle about a longitudinal axis of the needle;
a distal hub configured to be temporarily coupled to a terminal joint of the robotic arm, wherein the distal hub includes a passage for receiving the needle;
wherein the needle translator is configured to translate the needle through the distal hub and translate the proximal hub towards the distal hub;
a tissue chamber being established at least in part by a hollow interior of the needle and in fluidic communication with a vacuum source;
wherein the needle can be axially translated and rotated relative to the longitudinal axis of the needle while the tissue chamber is subject to a vacuum.

15. The device of claim 14, wherein the proximal hub comprises:
a removable attachment mechanism;
a luer hub retention latch; and
an interface for transferring oscillatory and translational motion from the motor to the needle gear.

16. The device of claim 14, further including an anti-buckling tube extending at least partially between the distal hub and the proximal hub, wherein the needle passes through the anti-buckling tube and the anti-buckling tube has greater rigidity than the needle.

17. The device of claim 14, wherein the distal hub comprises:
a removable attachment mechanism;
a sheath clamping latch;
a guide tube; and
an endoscope.

18. The device of claim 14, further comprising sensors, including:
a position sensor configured to monitor movement of the robotic arm;
a pressure sensor configured to monitor vacuum levels within the tissue chamber; and
a force-torque feedback sensor configured to monitor the rotation and translation of the needle.

* * * * *